(12) United States Patent
Barraclough et al.

(10) Patent No.: US 7,138,427 B2
(45) Date of Patent: Nov. 21, 2006

(54) 5-β-SAPOGENIN AND PSEUDOSAPOGENIN DERIVATIVES AND THEIR USE IN THE TREATMENT OF DEMENTIA

(75) Inventors: Paul Barraclough, Maidstone (GB); Jim Hanson, West Sussex (GB); Phil Gunning, Grantchester (GB); Daryl Rees, Sandy (GB); Zongqin Xia, Shanghai (CN); Yaer Hu, Shanghai (CN)

(73) Assignee: Phytopharm PLC., Godmanchester (GB)

( * ) Notice: Subject to any disclaimer, the term of this patent is extended or adjusted under 35 U.S.C. 154(b) by 69 days.

(21) Appl. No.: 10/109,095

(22) Filed: Mar. 28, 2002

(65) Prior Publication Data

Related U.S. Application Data

(63) Continuation-in-part of application No. PCT/GB00/03737, filed on Sep. 29, 2000, which is a continuation-in-part of application No. 09/647,110, filed as application No. PCT/GB99/00951 on Mar. 26, 1999, now abandoned.

(30) Foreign Application Priority Data

Sep. 29, 1999 (GB) .................................. 9923076.5

(51) Int. Cl.
*A61K 31/35* (2006.01)
*C07D 493/20* (2006.01)

(52) U.S. Cl. ...................... 514/453; 514/468; 549/344; 549/456

(58) Field of Classification Search ................ 549/344, 549/456; 514/453, 468
See application file for complete search history.

(56) References Cited

U.S. PATENT DOCUMENTS

| | | | |
|---|---|---|---|
| 3,836,527 A | 9/1974 | Irmscher et al. .... 260/239.55 A |
| 3,890,438 A | 6/1975 | Cayen et al. ................ 424/240 |
| 3,929,769 A | 12/1975 | Kaufmann et al. . 260/239.55 R |
| 3,956,491 A | 5/1976 | Isaac .......................... 424/241 |
| 4,482,706 A | 11/1984 | Tomimatsu et al. .......... 536/6.1 |
| 4,546,097 A | 10/1985 | Pitha ........................... 514/26 |
| 4,562,250 A | 12/1985 | Staba et al. ..................... 536/6 |
| 4,602,003 A | 7/1986 | Malinow ...................... 514/26 |
| 4,602,005 A | 7/1986 | Malinow ...................... 514/26 |
| 4,680,289 A | 7/1987 | Applezweig ................ 514/172 |
| 4,800,080 A | 1/1989 | Grollier et al. ................ 424/74 |
| 5,002,939 A | 3/1991 | Streber ........................ 514/173 |
| 5,017,562 A | 5/1991 | Holmes et al. ............... 514/26 |
| 5,244,887 A | 9/1993 | Straub ........................ 514/182 |
| 5,252,729 A | 10/1993 | De Crosta et al. ............. 540/18 |
| 5,589,182 A | 12/1996 | Tashiro et al. ............... 424/423 |
| 5,629,295 A | 5/1997 | Deninno et al. ............... 514/26 |
| 5,698,526 A | 12/1997 | Deninno ...................... 514/26 |
| 5,703,052 A | 12/1997 | Deninno et al. ............... 514/26 |
| 5,760,009 A | 6/1998 | Allen et al. ................... 514/26 |
| 5,763,430 A | 6/1998 | Zasloff ........................ 514/169 |
| 5,792,635 A | 8/1998 | Zasloff ........................ 435/184 |
| 5,795,885 A | 8/1998 | Zasloff et al. .............. 514/182 |
| 5,804,239 A | 9/1998 | Wiersma ..................... 426/302 |
| 5,804,562 A | 9/1998 | Allen et al. ................... 514/26 |
| 5,807,834 A | 9/1998 | Morehouse ................... 514/26 |
| 5,840,740 A | 11/1998 | Zasloff et al. .............. 514/182 |
| 5,840,936 A | 11/1998 | Zasloff et al. .............. 552/521 |
| 5,847,172 A | 12/1998 | Zasloff et al. .............. 552/521 |
| 5,856,535 A | 1/1999 | Zasloff et al. .............. 552/521 |
| 5,939,398 A | 8/1999 | Deninno ....................... 514/26 |
| 5,958,770 A | 9/1999 | Cham et al. ................. 435/375 |
| 6,046,184 A | 4/2000 | Suzuki et al. ................ 514/177 |
| 6,143,738 A | 11/2000 | Zasloff ........................ 514/181 |
| 6,150,336 A | 11/2000 | Deninno et al. .............. 514/26 |
| 6,258,386 B1 | 7/2001 | Xia et al. .................... 424/725 |
| 6,593,301 B1 | 7/2003 | Ma et al. ...................... 514/26 |
| 6,812,213 B1 | 11/2004 | Xia et al. ..................... 514/26 |
| 2001/0024666 A1 | 9/2001 | Waggle et al. .............. 424/757 |
| 2001/0026814 A1 | 10/2001 | Waggle et al. .............. 424/757 |
| 2001/0029248 A1 | 10/2001 | Waggle et al. ................ 514/27 |
| 2001/0043955 A1 | 11/2001 | Xia et al. .................... 424/725 |
| 2002/0018811 A1 | 2/2002 | Penteado et al. ........... 424/474 |

FOREIGN PATENT DOCUMENTS

| | | |
|---|---|---|
| CN | 1096031 A | 5/1993 |
| CN | 1102186 A | 10/1993 |
| CN | 1092991 A | 10/1994 |
| CN | 1092992 A | 10/1994 |
| DE | 4303214 A1 | 2/1993 |
| EP | 0 054 570 | 6/1982 |
| EP | 1020477 | 7/2000 |
| EP | 1024146 A1 | 8/2000 |
| FR | 2 743 561 | 1/1996 |
| GB | 852847 | 11/1960 |
| GB | 2 097 672 | 10/1982 |
| GB | 2335599 B | 9/1999 |

(Continued)

OTHER PUBLICATIONS

Kenney H.E. and Wall M.E., "Steroidal Sapogenins, XLI. Willagenin, a New 12-Keto Sapogenin", J. Org. Chem., 22:468-469 (1957).

(Continued)

*Primary Examiner*—Kamal A. Saeed
(74) *Attorney, Agent, or Firm*—Marshall, Gerstein & Borun LLP

(57) ABSTRACT

The invention discloses the use of sapogenin derivatives in the treatment of cognitive disfunction and similar conditions. Methods of treatment and pharmaceutical compositions are also disclosed

27 Claims, 4 Drawing Sheets

FOREIGN PATENT DOCUMENTS

| | | |
|---|---|---|
| GB | 2347676 A | 9/2000 |
| JP | 62-234025 | 10/1987 |
| JP | 02-188528 | 7/1990 |
| JP | 05-246866 | 9/1993 |
| JP | 09-100295 | 4/1997 |
| WO | WO 92/13873 | 8/1992 |
| WO | WO 94/18994 | 1/1994 |
| WO | WO 94/25017 | 11/1994 |
| WO | WO 95/30341 | 11/1995 |
| WO | WO 96/04296 | 2/1996 |
| WO | WO 97/31933 | 9/1997 |
| WO | WO 98/03180 | 1/1998 |
| WO | WO 98/51302 | 11/1998 |
| WO | WO 98/58543 | 12/1998 |
| WO | WO 98/58650 | 12/1998 |
| WO | WO 99/09837 | 3/1999 |
| WO | WO 99/16449 | 4/1999 |
| WO | WO 99/16786 | 4/1999 |
| WO | WO 99/48482 | 9/1999 |
| WO | WO 99/48507 | 9/1999 |
| WO | WO 00/61153 | 10/2000 |
| WO | WO 01/23406 A1 | 4/2001 |
| WO | WO 01/23407 A1 | 4/2001 |
| WO | WO 01/23408 A1 | 4/2001 |
| WO | WO 01/49703 A2 | 7/2001 |

OTHER PUBLICATIONS

Marker R.E., Wagner R.B., Ulshafer P.R., Wittbecker E.L., Goldsmith D.P.J., and Ruof C.H., "Sterols. CLVII. Sapogenins. LXIX. Isolation and Structures of Thirteen New Steroidal Sapogenins. New Sources for Known Sapogenins.", J. Am. Chem. Soc., 65:1199-1209 (1943).

Wall M.E. and Serota S., "Steroidal Sapogenins. XLV. Effect of Side Chain Isomerism on Rate of Conversion to Pseudosapogenins", J. Am. Chem. Soc., 79:6481-6483 (1957).

Farmer SN and Kon GAR, "Sapogenins. Part II. Sarsasapogenin and Smilagenin" Journal of the Chemical Society (1937) pp. 414-420.

Marker RE, Rohrmann E and Jones EM, "Sterols. XCIII. epi-Pseudosarsasapogenin, Pseudosarasapogenine and Pseudochlorogenin" Journal of the American Chemical Society vol. 62, No. 3 (1940) pp. 648-649.

Marker RE, Turner DL, Ulshafer PR, "Sterols. CXLVIII. Sapogenins. LXII. The Structure of the Side Chain in the Dihydropseudosapogenins" Journal of the American Chemical Society vol. 64 (1942) pp. 1655-1658.

Marker RE, Wagner RB, Ulshafer PR, Wittbecker EL, Goldsmith DPJ and Ruof CH, "Steroidal Sapogenins" Journal of the American Chemical Society vol. 69, No. 9 (1947) pp. 2167-2230.

Wendler NL, Slates HL and Tishler M, "The transformation of Manogenin to Hecogenin" Journal of the American Chemical Society vol. 74, No. 19 (1952) pp. 4894-4897.

6001 Chemical Abstracts, Columbus, Ohio, US, vol. 49 Oct. 11, 1955 No.21 [full reference: J. Pharm. Soc. Japan 74, 1165-7 (1954)].

Wall ME, Serota S and Eddy CR, "Steroidal Sapogenins. XVII. Sterochemistry of the Spioketal Side Chain" Journal of the American Chemical Society vol. 77 (1955) pp. 2130-1237.

Djerassi C and Fishman J, "Constitution and Stereochemistry of Samogenin, Markogenin and Mexogenin" Journal of the American Chemical Society vol. 77, No. 16 (1955) pp. 4291-4297.

Ziegler JB, Rosen WE and Shabica AC, "The Stereochemistry of Steroidal Sapogenins II" Journal of the American Chemical Society vol. 77, No. 5 (1955) pp. 1223-1229.

Scheer I, Kostic RB and Mosettig E, "The C-25 Isomerism of Smilagenin and Sarsasapogenin" Journal of the American Chemical Society Scheer I, Kostic RB and Mosettig E, "The C-25 Isomerism of Smilagenin and Sarsasapogenin" Journal of the American Chemical Society vol. 77, No. 3 (1955) pp. 641-646.

Elks J, Phillipps GH, Walker T and Wyman LJ, "Studies in the Synthesis of Cortisone. Part XV. Improvements in the Conversion of Hecogenin into 3β : 12β-Diacetoxy-5α: 25D-spirostan-11-one and a Study of the Isomeric 11 : 12-Ketols" Journal of the Chemical Society (Nov. 1956) pp. 4330-4331.

6001 Chemical Abstracts, Columbus, Ohio US, vol. 51 Aug. 25, 1957 No. 16 [full reference: J. Chem. Soc. 1957, 1175-85; cf. C.A. 51,6673f].

Takeda K and Hamamoto K, "The Structure of Metagenin" Tetrahedron Letters No. 3 (1960) pp. 1-8.

6001 Chemical Abstracts, Columbus, Ohio US, vol. 54 Nov. 25, 1960 No. 22 [full reference: Chem. and Pharm. Bull. (Tokyo) 7, 343-8 (1959)].

Hamamoto K, "Steroidal components of domestic plants. XXIV. Structure of metagenin. 4" Chemical and Pharmaceutical Journal (Tokyo) 9 (1961) pp. 32-37.

Pettit GR and Kasturi TR, "Steroids and Related Natural Products. VII. Boron Triflouride Etherate-Lithium Aluminium Hydride Reduction of Smilagenin Acetate" Journal of Organic Chemisty vol. 26 (1961) pp. 4553-4556.

6001 Chemical Abstracts, Columbus, Ohio US, vol. 59 Nov. 25, 1963 No. 11 [full reference: Hua Hsuek Pao 28 (6), 394-7 (1962)].

6001 Chemical Abstracts, Columbus, Ohio US, vol. 59 Sep. 2, 1963 No. 5 [full reference: Chem. and Pharm. Bull. (Tokyo) 11, 139-44 (1963)].

Bedour MS, El-Minajjed D, Fayez MBE and Girgis AN, "Steroid Sapogenins VII. Identification and Origin of 25D-Spirosta-3,5-diene Among the Fenugreek Sapogenins" Journal of Pharmaceutical Sciences vol. 53, No. 10 (1964) pp. 1276-1278.

6001 Chemical Abstracts, Columbus, Ohio US, vol. 63 Dec. 20, 1965 No. 13 [full reference: Chem. and Pharm. Bull. (Tokyo) 11, 95-103 (1963)].

Schreiber K, Ripperger H, and Budzikiewicz H, "(22R:25S)-3β-Amino-5α-spirostan, ein Steroidalkaloid Neuartigen Strukturtyps aus Solanum Paniculatum L." Tetrahedron Letters No. 45 (1965) pp. 3999-4002.

Schreiber K and Ripperger H, "Jurubine, A Novel Type of Steroidal Saponin with (25S)-3β- amino-5α-furostane-22α.26-diol 0(26)-β-D-glucopyranoside structure from solanum paniculatum L." Tetrahedron Letters No. 45 (1965) pp. 5997-6002.

6001 Chemical Abstracts, Columbus, Ohio US, vol. 64 Mar. 14, 1996 No. 6 [full reference: Ciencia (Mex.) 24 (1-2), 89-92 (1965)].

Takeda K, Lukacs G and Yasuda F, "Studies on the Steroidal Components of Domestic Plants. Part LIV" Journal of the Chemical Society, Section C (1968) pp. 1042-1044.

Gandolfi C, Doria G and Longo R, "(20βH, 22αO, 25R)-5α-Spirostan-3β-amino-6α-Ol and its Isomers" Tetrahedron Letters No. 19 (1970) pp. 1677-1680.

Cambiaghi S, Dradi E and Longo R, "Struttura e configurazione assoluta di nuovi alcaloidi del Solanum paniculatum L" Annali Di Chimica, vol. 61, No. 1 (1971) pp. 99-111.

Guseinov D and Iskenderov GB, "Chemical composition and biological value of saponins of some plants of Azerbaidzhan" Azerb. Med. Inst., Baku, USSR (1972).

Albert AH, Pettit GR and Brown P, "Reduction of the Steroidal Sapogenin Spiro Ketal System" Journal of Organic Chemistry vol. 38, No. 12 (1973) pp. 2197-2201.

Tschesche R, Saito Y and Topfer A, "Synthese von (25S)-16β, 26-Dihydroxycholesterol und (25S)-16β, 26-Dihydroxy-5-Cholestanol" Tetrahedron Letters No. 12 (1974) pp. 967-970.

Sykes PJ, Whitehurst JS, "Steriod synthesis" Terpenoids Steroids (1976), 6, pp. 276-343, especially 335 and 336.

Blunden G, Yi Y and Jewers K, "Steroidal Sapgenins from Leaves of Agaveae Species" Sch. Pharm., Portsmouth Polytech., UK (1979).

Zachis M and Rabi J, "The Clemmensen Reaction of Tigogenin. A Reinvestigation" Tetrahedron Letters vol. 21 (1980) pp. 3735-3738.

Irismetov MP, Goryaev MI, Bazalitskaya VS and Kairgalieva AK, "Modified steroids. XVI. Study of the Leuckart reaction in a series of steroid compounds of solasodine and diosgenin" Inst. Khim. Nauk, Alma-Ata, USSR (1980).

Barton DHR, Bringmann G et al., "Reactions of Relevance to the Chemistry of Aminoglycoside Antitbiotics. Part 14. A Useful Radical-deamination Reaction" J. Chem. Soc., Perkin Trans. 1 (1980) pp. 2657-2664.

Dawidar AM, Saleh AA, Abdel-Galil and Abdel-Malek MM, "Keto-Steriods, I, Conversion of Diosgenin to 6β-methylpregn-4-ene-6α,20-diol-3, 16-dione" Zeitschrift Fuer Naturforschung, Tiel B: Anorganische Chemie, Organische Chemie, De, Verlag Der Zeitschriften Fuer Naturforschung, vol. 37B, No. 1 (1982) pp. 892-895.

6001 Chemical Abstracts, Columbus, Ohio US, vol. 97 Aug. 16, 1982 No. 7 [full reference: Vopr. Med. Khim. (1982), 28(3), 101-5 (Russ)].

Milkova T, Stein H, Ponty A, Böttger D and Welzel P, "14β-Hydroxy Steroids—VI. Synthesis of Digitoxigenin" Tetrahedron Letters vol. 23, No. 4 (1982) pp. 413-414.

Chakravarty AK, Das B, Pakrashi SC, "Juripidine A 3 Amino Steroidal Alkaloid from Roots of Solanum-Hispidum" Pyhtochemistry (Oxford) (1983), pp. 2843-2846.

Schwartz RD, Lehmann J, Kellar KJ, "Presynaptic Nicotinic Cholinergic Receptors Labeled by [$^3$H] Acetylcholine on Catecholamine and Serotonin Axons in Brain" Journal of Neurochemistry, New York (1984), pp. 1495-1498.

Wang S-Z, Hu J, Long RM, Pou WS, Forray C, and El-Fakahany EE, "Agonist-induced down-regulation of m1 muscarinic receptors and reduction of their mRNA level in a transfected cell line" Federation of European Biochemical Societies Letters vol. 276, No. 1, 2 (1990) pp. 185-188.

Ding Y, Yi N, Wang Y, Dai X, Xia Z, Study on the "Yin-tonic" component of the Chinese herb Zhimu: Sarsasapogenin" Hejishu (1991), 14 (5), 262-5.

Coll PF, Rodriguez ML, Perez C, Adam G, "Steroidal compounds of Solanum atillarum O. E. Schulz. II" Rev. Cubana Quim. (1992), 6(2), 66-71.

Fukamauchi F, Saunders PA, Hough C, and Chuang D, "Agonist-Induced Down-Reglulation and Antagonist-Induced Up-Regulation of $m_2$- and $m_3$- Muscarinic Acetylcholine Receptor mRNA and Protein in Cultured Cerebellar Granule Cells" Molecular Pharmacology (1993) pp. 940-949.

DeNinno MP, "Anomalous Ozonolysis of Cyclic Allylic Alcohols: Mechanism and Synthetic Untility", J. Am. Chem. Soc. 117 (1995) pp. 9927-9928.

Luming H, Ya'er H, Yi N, Xia Z, "The mechanism of the regulatory action of sarsasapogenin on brain M-receptors in aged mice", Shanghai Dier Yike Daxue Xuebao 16 (5) (1996) pp. 346-349.

Hu Y, Yi N, He L, et al, "An autoradiographic study on the regional distribution of brain M-cholinergic receptors in aged rats", (1996) Chinese Journal of Gerontology vol. 15(2).

Lorizzi M, DeMarino S, Minale L, Zollo F, LeBert V, Roussakis C, "Investigation of the polar steroids from an Antarctic Starfish of the family Echinasteridae: isolation of twenty seven polyhydroxysteroids and steroidal oligoglycosides, structures and biological activities.", Tetrahedron Letters vol. 52, No. 33 (1996) pp. 10997-11012.

DeNinno MP, McCarthy KE, "The $^{14}$C Radiolabelled Synthesis of the Cholesterol Absorption Inhibitor CP-148, 623. A Novel Method for the Incorporation of a $^{14}$C Label in Enones", Tetrahedron Letters vol. 53, No. 32 (1997) pp. 11007-11020.

Yi N, Hu Y, Xia Z, "Sarsasapogenin: Mechanism in Treating Senile Dementia", Systhesis and Applications of Isotopically Labelled Compounds (1997) pp. 315-320.

Yi N, Hu Y, Xia Z, "The Mechanism of a Sapogenin from Anemarrhenae Asphodeloides BGE in the Treatment of Senile Dementia", Collection of Abstract prepared for the 6$^{th}$ International Symposium of the International Isotope Society, Philadelphia, Sep. 14-18, 1997, p. 103.

DeNinno P, McCarthy PA, Duplantier KC, Eller C, et al, "Steroidal Glycoside Cholesterol Absorption Inhibitors", Journal of Medicinal Chemistry (1997) vol. 40, pp. 2547-2554.

Chang ZL, Puhl HL, May LG, Williams CL, and Aronstam RS, "Influence of Acute and Chronic Ethanol Treatment on Muscarinic Responses and Receptor Expression in Chinese Hamster Ovary Cells", Biochem Pharmacol 54,7 pp. 834-839 (1997).

Kinoshita K, Akiba M, Saitoh M, Ye Y, Koyama K, Takahashi K, Kondo N, and Yuasa H, "Antinociceptive Effect of Triterpenes from Cacti", Pharmaceutical Biology vol. 36, No. 1 (1998) pp. 50-55.

Fukamauchi F, Wang Y-J, Chuang D-M, "Ethanol Induces Subtype-Specific Up-Regulation of Muscarinic Acetylcholine Receptor mRNA in Neurohybrid Cell Lines", Life Sciences, vol. 62, No. 5 (1997) pp. 389-396.

Rahman, A-U, Choudhary MI, Asif F, Farooq A, Yaqoob M, and Dar A, "Microbial Transformation of Sarsasapogenin by Fusarium Lini", Phytochemistry vol. 49, No. 8 (1998) pp. 2341-2342.

Sramek JJ, Forrest M, Mengel H, Jhee SS, Hourani J, and Cutler NR, "A Bridging Study of Lu 25-109 in Patients with Probable Alzheimer's Disease", Life Sciences vol. 62, No. 3 (1998) pp. 195-202.

Betancor C, Dorta RL, Freire R, Martin A, Prange T and Suarez E, "Stereospecific Synthesis of 1,6-Dioxadecalins and 2,2'-Linked Ditetrahydrofurans by Rearrangement of Steroidal Spiroacetals" Journal of Organic Chemistry vol. 63 (1998) pp. 6355-6362.

Arteaga MAI, Martinez CSP and Manchado FC, "Synthesis and Characterization of (25R)-2α,3α-Epoxy-5α-Spirostan-12,23-Dione" Synthetic Communications, 29(11) (1999) pp. 1811-1818.

LaCour TG and Fuchs PL, "Concurrent Ring Opening and Halogenation of Spiroketals" Tetrahedron Letters 40 (1999) pp. 4655-4658.

5-β-SAPOGENIN AND PSEUDOSAPOGENIN DERIVATIVES AND THEIR USE IN THE TREATMENT OF DEMENTIA

RELATED APPLICATION

This application is a continuation-in-part of International Patent Application No. PCT/GB00/03737, filed 29 Sep. 2000, which is a continuation-in-part of Ser. No. 09/647,110 filed Jan. 11, 2001, now abandoned, which is a 371 of National Phase Application PCT/GB99/00951, filed Mar. 26, 1999.

The present invention relates to sapogenin derivatives and their use in treating cognitive disfunction and allied conditions; and to compositions for use in such treatments. The invention is also concerned with the treatment of conditions that are characterised by a deficiency in the number or function of membrane-bound receptors. In the following, the present invention will be described principally with reference to the treatment of Alzheimer's disease (AD) and senile dementia of the Alzheimer's type (SDAT), where deficiencies in a number of receptor types have been demonstrated. However, it is to be understood that the present invention relates generally to the treatment of conditions attributable to intrinsic pathological conditions and/or exposure to adverse environmental conditions these conditions being characterised by a deficiency in the number or function of membrane-bound receptors or a deficiency in transmission at the junctions between neurones or at the junctions of neurones and effector cells.

Conditions of the type mentioned above include Parkinson's disease, Lewi body dementia, postural hypotension, autism, chronic fatigue syndrome, Myasthenia Gravis, Lambert Eaton disease, diseases and problems associated with Gulf War Syndrome, occupational exposure to organophosphorus compounds and problems associated with ageing.

Alzheimer's disease (AD) and senile dementia of the Alzheimer's type (SDAT) are grave and growing problems in all societies where, because of an increase in life expectancy and control of adventitious disease, the demographic profile is increasingly extending towards a more aged population. Agents which can treat, or help in the management of, AD/SDAT are urgently required.

Age-associated memory impairment (AAMI) is a characteristic of older patients who, while being psychologically and physically normal, complain of memory loss. It is a poorly defined syndrome, but agents which are effective in treatment of AD/SDAT may also be of value in these patients.

Research into AD/SDAT is being carried out by traditional and conventional medical research methods and disciplines. In conventional medicine, there are several approaches to the treatment of AD/SDAT. It is known that the biochemical processes subserving memory in the cerebral cortex are (at least in part) cholinergically-mediated. Those skilled in the art will know that "cholinergically mediated" mechanisms may be directly attributable to acetylcholine acting on receptors, and these are direct effects. Other, clinically useful effects may also be caused by modulation of release of acetylcholine from pre-synaptic nerve endings or inhibition of enzymes that destroy acetylcholine. These modulating factors may be exerted through neurones where the mediator is non-cholinergic; these are referred to as indirect effects. Some attempts at treatment have focussed on the role of other mediators such as 5-hydroxytryptamine, which is a mediator in other areas of brain, such as the mid-brain nuclei. However, since fibres from these areas are projected forward into the cerebral cortex where the primary transmitter is acetylcholine, attention has focussed on the management of this mediator in the search for appropriate therapeutic agents.

Cholinergic strategies for the treatment of AD/SDAT have been directed at several points along the pathway of formation, synaptic release and removal of released acetylcholine.

One approach involves treatment with high doses of lecithin and other precursors of acetylcholine. This is of limited use in producing sustained improvements in cognitive performance.

Another approach involves the use of vegetable drugs such as Polygalae root extract, which has been shown to enhance choline-acetylcholine transferase (CAT) activity and nerve growth factor (NGF) secretion in brain. Oral administration of NGF has no effect on central nervous system neurons because it is a high molecular weight protein that cannot pass through the blood-brain barrier. However, agents which can pass through the blood-brain barrier and have a stimulating effect on NGF synthesis in the central nervous system have been proposed for the improvement of memory-related behaviour.

The results of a third clinical approach, which uses cholinesterase inhibitors such as tacrine hydrochloride, have been marginally more positive than the above. Substances obtained from plants used in Chinese and Western medicine, for example huperzine, galanthamine, and physostigmine have all been shown to be of some—although limited—benefit in the treatment of AD/SDAT in clinical studies and also in laboratory models. All of these substances are inhibitors of acetylcholine esterase (AChE). In patients with AD/SDAT, there may be reduced synthesis of acetylcholine (ACh), reduced efficiency in release of ACh from presynaptic stores, and a decrease in the number or function of postsynaptic ($M_1$) receptors. Reductions in pre-synaptic $M_2$ receptors have also been shown. The beneficial effect of AChE inhibitors is attributed to enhancement of acetylcholine levels at synapses in brain by slowing down the destruction of released transmitter.

Compositions which modulate cholinergic function are known to affect memory and recall. For example, nicotine stimulates nicotinic acetylcholine receptors, and the short lived memory enhancing effects of cigarette smoking are thought to be due to the effect of nicotine. Scopolamine, an antagonist of acetylcholine, will produce amnesia and impaired cognitive function manifesting in psychomotor tests as a prolongation of simple reaction times, possibly as a result of impaired attention, and is used for this purpose as an adjunctive analgesic treatment. The amnesic effect of scopolamine can be antagonised by nicotine.

There are two families of nicotinic receptor subtypes ($\alpha$ and $\beta$), and each includes four subgroups which differ in ligand specificity. The role of nicotinic receptors in the CNS is not well understood at the molecular level. It is possible that agents binding to nicotinic receptors may modify the rate of turnover at muscarinic receptor sites in brain. Nicotinic receptors are ligand-gated ion channels, and their activation causes a rapid (millisecond) increase in cellular permeability to $Na^+$ and $Ca^{++}$, depolarisation and excitation.

Another class of cholinergic receptors can be stimulated by muscarine. Such muscarinic (M) receptors are G protein-coupled receptors. Responses of muscarinic receptors are slower; they may be excitatory or inhibitory. They are not necessarily linked to changes in ion permeability. Five types of muscarinic receptors have been detected by cholinergic receptor cloning, and are designated as $m_1$–$m_5$. Pharmacological effects are associated with four of the cloned receptors and they are designated as $M_1$–$M_4$ based on pharmacological specificity.

Using specific receptor proteins and monoclonal antibodies, it has been possible to further localise muscarinic receptors in brain as $m_1$ (postsynaptic) and $m_2$ (presynaptic). In heart, $M_2$ receptors are postsynaptic. Presynaptic muscarinic receptors are thought to be inhibitory, the binding of ACh to these receptors attenuating the release of further ACh to provide a negative feedback mechanism for Ach release. Selective $M_2$ receptor antagonists which are preferentially distributed to the brain may therefore be useful in treating Alzheimer's disease.

It is known that, in disease states such as AD/SDAT, there is general neuronal loss and deficits in cholinergic nerve function. It has been speculated that the high affinity nicotinic binding sites in the remaining cholinergic neurons might be converted to low affinity binding sites in treating such diseases, thereby sustaining transmitter release. By lowering the affinity of the nicotinic binding sites, a quick desensitising process is avoided.

Agonist activation at nicotinic receptors in brain has rapid onset and offset. A decreased affinity of the nicotinic receptors will reduce the desensitisation process. Schwarz R. D. et al (J. Neuro Chem 42, (1984), 1495–8) have shown that nicotine binding sites are presynaptically located on cholinergic (and also 5-hydroxytryptaminergic and catecholaminergic) axon terminals. A change in high affinity binding sites on AD/SDAT may also induce a change in the modulatory effect the nicotinic binding sites may have on other transmitter systems.

Presynaptic cholinergic mechanisms are also under inhibitory control by GABAergic neurons and this inhibition is thought to be intensified in AD/SDAT. Removal or reduction of this inhibition intensifies presynaptic cortical cholinergic activity and enhances cognitive processing.

The interactions of interneuronal fibres innervated by nicotine (reducing binding affinity), and dis-inhibition of GABAergic fibres both have a presynaptic locus.

This is a simplistic model of central transmission, but provides a framework for understanding the attempts which have been made to increase the effective concentration of acetylcholine in central synapses. This further illustrates the concept of direct and indirect action. There are disadvantages attaching to the three conventional therapeutic approaches to AD/SDAT treatment mentioned above: ACh precursor supplementation, agonist replacement and acetylcholine esterase inhibition. These treatments may result in a short-term increase in the availability of ACh which may activate feedback mechanisms resulting in the desensitisation of postsynaptic receptors. On theoretical grounds, long term benefits would not be predicted and when treatment is interrupted, any benefits in management of AD/SDAT and AAMI disappear and the condition may even be aggravated.

It has been shown that a compound with $M_1$ agonist and $M_2/M_3$ antagonist activity improved cognitive performance in SDAT patients (Sramak et al, Life Sciences vol. 2, No. 3, 195–202, 1997). However, this compound causes unacceptable cholinergic side effects, such as fatigue, diarrhoea and nausea.

A more radical approach to AD/SDAT and AAMI aims to increase the number of postsynaptic ($M_1$) receptors, in brain. It is known from Chinese Patent No. CN1096031A, that sarsasapogenin (SaG) can upregulate $M_1$ cholinergic receptors.

Patent applications have been published which claim the usefulness of a number of steroid sapogenins having spirostane, furo-spirostane, spirosolane or solanidine structures in the treatment of disease. Two patent publications are of particular relevance here: Chinese Patent Application No. CN1096031A discloses two-way regulatory effects of the spirostane sapogenin, sarsasapogenin, on β-adrenergic and M-cholinergic receptors. The disclosure in this document, however, is brief. The other document of relevance is patent publication DE 4303214A1 which claims the use of a very wide range of saponins and sapogenins in the treatment of a whole range of diseases that the inventors consider to be of viral origin. This disclosure is however of dubious value in that it is well recognised that there is no infective element to a very large number of the conditions that are characterised by deficient synaptic transmission and thus the basic premise of the alleged invention is flawed. In addition they present no data of any kind that allows one skilled in the art to be able select a preferred compound from the large number that are claimed.

The inventors have found that certain sapogenin derivatives exhibit the ability to regulate receptors. In particular, these compounds have been found to increase the number of M2 receptors in the brain. Thus, according to one aspect of the invention, there is provided the use of a sapogenin derivative of general formula (I) or (II) in the manufacture of a medicament for the treatment of a condition characterised by a deficiency in membrane-bound receptor number or function.

Those skilled in the art will be aware of the relationship between saponins and their sapogenins, and that the latter tend to be fat-soluble whereas the saponins tend to be water-soluble. Sapogenins are therefore better able to cross the blood-brain barrier. The skilled man will also be aware of the epimerisation of certain sapogenins under conditions of acid hydrolysis.

The variation in pharmacological properties and pharmacodynamic actions of various types of sapogenins underlines the need for selection of those agents which are most useful in the treatment of AD/SDAT. The discovery of novel facts about the action of sapogenin derivatives has made it possible to determine which substances are most useful for the treatment of AD/SDAT and the like.

The inventors have found that the above-described properties are exhibited by sapogenin derivatives wherein the A/B ring conformation of the fused ring system is Cis.

Accordingly, the sapogenin derivatives of interest in this invention have the following general formulas (I) or (II):

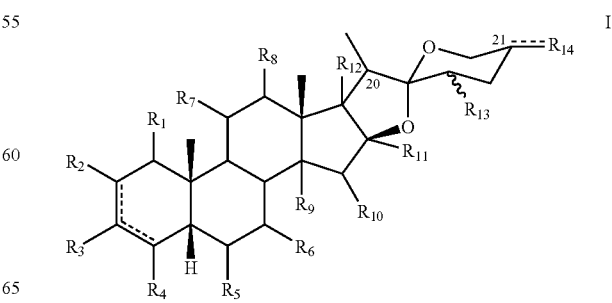

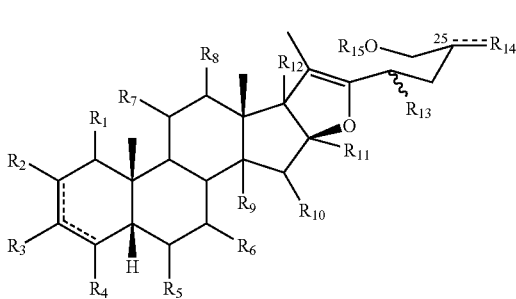

and their stereoisomers and racemic mixtures, their pharmaceutically acceptable pro-drugs and salts.

In the general Formula (I):

$R_1$, $R_2$, $R_3$, $R_4$, $R_5$, $R_6$, $R_7$, $R_8$, $R_{10}$, are, independently of each other, either H, OH, =O, and OR where R=optionally substituted alkyl, optionally substituted acyl, optionally substituted carbamoyl, alkoxycarbonyl;

$R_9$, $R_{12}$, $R_{11}$, $R_{13}$ can be either a H, OH, OR where R=optionally substituted alkyl, optionally substituted acyl, optionally substituted carbamoyl, alkoxycarbonyl;

$R_{14}$=optionally substituted alkyl group,

====represents an optional double bond, but excluding where simultaneously:

$R_1=R_2=R_4=R_5=R_6=R_7=R_8=R_{10}=R_{11}=R_9=R_{12}=R_{13}=H$,
$R_3=\beta OH$,
$R_{14}=CH_3$
the methyl group at C22 is $\alpha$,
the C20 is $\alpha$, and there is a S configuration at C25.

Preferably, in the general formula (I):

$R_4$, $R_9$, $R_{12}$, $R_{13}$=H $R_1$, $R_2$, $R_3$, $R_5$, $R_6$, $R_7$, $R_8$, $R_{10}$, can be independently of each other either H, OH, =O, OR where R=optionally substituted alkyl, optionally substituted acyl, optionally substituted carbamoyl, alkoxycarbonyl;

$R_{11}$=H, OH, OR where R=optionally substituted alkyl, optionally substituted acyl, optionally substituted carbamoyl, alkoxycarbonyl;

$R_{14}$=optionally substituted alkyl group and ====represents an optional double bond, but excluding where simultaneously:

$R_1=R_2=R_4=R_5=R_6=R_7=R_8=R_{10}=R_{11}=R_9=R_{12}=R_{13}=H$,
$R_3=\beta OH$,
$R_{14}=CH_3$,
the methyl group at C22 is $\alpha$,
the C20 is $\alpha$, and there is a S configuration at C25.

More preferably, in the general formula (I):

$R_1=R_2=R_4=R_5=R_6=R_7=R_8=R_{10}=R_{11}=R_9=R_{12}=R_{13}=H$,
$R_3=H$, —OH, —OMe, —OCOCH$_3$, =O, —O—CO—OEt, —O—CO—(CH$_2$)$_2$—CO$_2$H
$R_{14}=CH_3$, but excluding where simultaneously $R_1=R_2=R_4=R_5=R_6=R_7=R_8=R_{10}=R_{11}=R_9=R_{12}=R_{13}=H$,
$R_3=\beta OH$,
$R_{14}=CH_3$,
there is a S configuration at C25,
the C20 is $\alpha$ and the methyl group at C22 is $\alpha$.

In the general formula (II):

$R_1$, $R_2$, $R_3$, $R_4$, $R_5$, $R_6$, $R_7$, $R_8$, $R_{10}$, are, independently of each other, either H, OH, =O, or OR where R=optionally substituted alkyl, optionally substituted acyl, optionally substituted carbamoyl, alkoxycarbonyl;

$R_9$, $R_{12}$, $R_{11}$, $R_{13}$ can be either a H, OH, OR where R=optionally substituted alkyl, optionally substituted acyl, optionally substituted carbamoyl, alkoxycarbonyl;

$R_{14}$=optionally substituted alkyl group;

$R_{15}$=H, optionally substituted alkyl, optionally substituted acyl, or glucosyl;

====represents an optional double bond.

Preferably, in the general formula (II):

$R_4$, $R_9$, $R_{12}$, $R_{13}$=H $R_1$, $R_2$, $R_3$, $R_5$, $R_6$, $R_7$, $R_8$, $R_{10}$, can be independently of each other either H, OH, =O, OR where R=optionally substituted alkyl, optionally substituted acyl, optionally substituted carbamoyl, alkoxycarbonyl;

$R_{11}$=H, OH, OR where R=optionally substituted alkyl, optionally substituted acyl, carbamoyl, alkoxycarbonyl;

$R_{14}$=optionally substituted alkyl group $R_{15}$=H, optionally substituted alkyl, optionally substituted acyl, or glucosyl;

and ====represents an optional double bond.

The following compounds are particularly preferred:

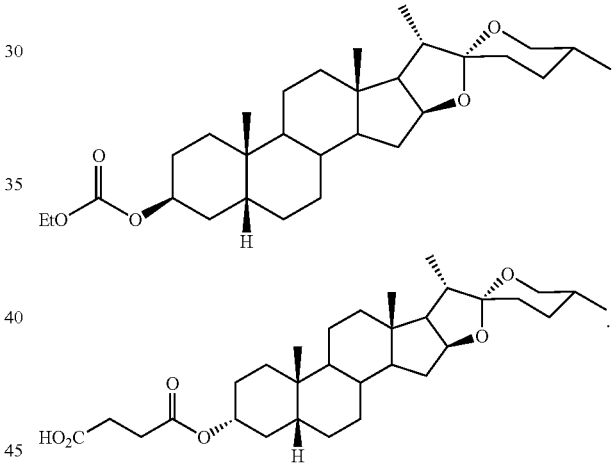

As used hereabove and hereafter:

"Acyl" means an H—CO— or Alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. Exemplary alkyl groups include methyl, ethyl, n-propyl, i-propyl, n-butyl, t-butyl, n-pentyl, 3-pentyl.

"Optionally substituted" means that the said group may be substituted with one or more substituents which may be the same or different, and include halo, alkyl, cycloalkyl, hydroxy, alkoxy, amino, acylamino, aryl, aroylamino, carboxy, alkoxycarbonyl, aralkoxycarbonyl, heteroaralkoxycarbonyl, optionally substituted carbamoyl.

The term "pharmaceutical composition" means a composition comprising a compound of formula I or II and at least one component selected from the group comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

"Pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

"Pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington, Pharmaceutical Sciences, Mack Publishing Co., Easton, Pa., latest edition.

"Pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. Because of the ease with which the metabolically cleavable groups of the compounds useful according to this invention are cleaved in vivo, the compounds bearing such groups act as pro-drugs. A thorough discussion of prodrugs is provided in the following: Design of Prodrugs, H. Bundgaard, ed., Elsevier, 1985; Methods in Enzymology, K. Widder et al, Ed., Academic Press, 42, p. 309–396, 1985; A Textbook of Drug Design and Development, Krogsgaard-Larsen and H. Bundgaard, ed., Chapter 5; Design and Applications of Prodrugs p. 113–191, 1991; Advanced Drug Delivery Reviews, H. Bundgard, 8, p. 1–38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. See, for example S. M. Berge, et al., Pharmaceutical Salts, J. Pharm. Sci., 66: p. 1–19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts.

Some sapogenin derivatives of interest in the present invention may occur naturally in a range of plant species, notably from the genera *Smilax, Asparagus, Anemarrhena, Yucca* and *Agave*. The species presently of greatest interest include *Smilax regelii* Kilip & Morton—commonly known as *Honduran sarsaparilla; Smilax aristolochiaefolia* Miller—commonly known as Mexican sarsaparilla; *Smilax ornata* Hooker—commonly known as Jamaican *sarsaparilla; Smilax aspera*—commonly known as Spanish *sarsaparilla; Smilax glabra* Roxburgh; *Smilax febrifuga*—Kunth—commonly known as Ecuadorian or Peruvian sarsaparilla; *Anemarrhena asphodeloides* Bunge; *Yucca schidigera* Roezl ex Ortgies; and *Yucca brevifolia* Engelm. Sapogenin derivatives which may be of interest may also occur naturally in other genera, for example *Dioscorea, Trillium, Solanum, Strophanthus,* Digitalis and Trigonella. However, some sapogenin derivatives from these sources possess undesirable properties and are thus not recommended for use in the invention.

Sapogenin derivatives of the invention may also be commercially available; suppliers are well-known from the one skilled in the art and may include Sigma Aldrich, Research Plus Inc., Steraloids Inc., etc.

According to a further aspect of the invention, there is provided a process of preparation of the compounds of the invention.

Substitued sapogenins of the present invention may be prepared by synthetic methods. For instance, they may be prepared from unsubstituted sapogenin derivatives, which may occur naturally or be commercially available, as stated above.

Starting from these unsubstituted sapogenins, the reaction may involve at least one substitution step, wherein the functional group is substituted on the sapogenin derivative; usually, the starting product is an unsubstituted sapogenin having the required sterechemistry, and the reaction may involve the substitution of one OH— group by the functional radical desired; smilagenin and epismilagenin are preferred as starting products.

Compounds useful according to the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy or carboxy groups, where these are desired in the final product, to avoid their unwanted participation in the reactions. Conventional protecting groups may be used in accordance with standard practice, for examples see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well techniques, such as recrystallization, reprecipitation or the various chromatography techniques, notably column chromatography or preparative thin layer chromatography.

According to a further aspect of the present invention, there is provided a pharmaceutical composition having cognitive function enhancing properties which comprises an effective amount of a sapogenin derivative of the invention.

In a still further aspect, the sapogenin derivatives of the present invention are steroidal; they are preferably non-oestrogenic in effect.

In another aspect, the invention provides a pharmaceutical composition having cognitive function enhancing properties which comprises an effective amount of a sapogenin derivative of the invention in the form of an extract derived from a plant of the genus *Smilax, Asparagus, Anemarrhena, Yucca* or *Agave*.

It will be appreciated that the invention embraces within its scope the use of the compositions defined above. Thus, according to a fifth aspect, the present invention provides a method of enhancing cognitive function which comprises administering to a human or animal an effective dosage of a composition of the invention.

The invention also provides a method of enhancing cognitive function in a human or non-human animal, which comprises administering an effective dose of sapogenin derivatives of the invention. Also, it concerns the use of the sapogenin derivatives of the invention in food product or beverage for enhancing cognitive function.

As used herein, the term "cognitive function" refers to functions such as thinking, reasoning, remembering, imagining and learning.

According to a further aspect, the invention also relates to composition having cognitive function enhancing properties which comprises at least two, preferably two, sapogenin derivatives of the invention.

In identifying compounds that would have use in the treatment of SDAT and other diseases characterised by reductions in receptor numbers or synaptic transmission, the inventors have given consideration to the need to identify compounds that would have the desired effect but would be devoid of any oestrogenic effects, as these would be unacceptable, particularly in male patients. A number of the compounds claimed to have activity in patent application DE 4303214A1 have marked oestrogenic activity and are therefore unacceptable. Preferably, sapogenin derivatives of the present invention however, does not display oestrogenic activity. In addition these compound were tested at other steroid receptors and were found to have no activity at any of the following receptors:

Progesterone

Glucocorticoid

Testosterone

Sapogenin derivatives of the present invenion have also been tested for activity in a number of in-vitro assays. The assays/experiments that were considered of key importance in determining possible activity in the elevation of membrane bound receptor numbers were as follows:

Chinese hamster ovary (CHO) cells transfected with the a DNA fragment coding for a muscarinic receptor. The cell line used for the majority of the experiments was a cell line expressing the m2 receptor.

The methods and the results of these experiments are now described in turn.

CHO Cell Line Experiments

The effects of various compounds on the expression of m2 receptors on CHO cells transfected with DNA for the m2 receptor were investigated. Receptor numbers were assayed using tritiated QNB binding and subtracting non-specific binding. Compounds were dissolved in DMSO and DMSO was used as a control. Compounds were tested at a range of final concentrations. Compounds were also tested in the presence and absence of tamoxifen to try to distinguish an oestrogen receptor mediated mechanism.

Compounds are active when the effect on receptor expression given as a percentage increase compared to control is more than 15%.

The results are summarised in the Table 1 below.

TABLE 1

Effects of sapogenin derivatives on the expression of $m_2$ receptors on CHO cells

| Compound | Molar concentration | Activity |
|---|---|---|
| 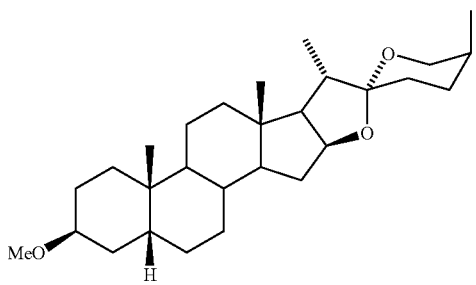 | $10^{-5}$ | Active |

TABLE 1-continued
Effects of sapogenin derivatives on the expression of $m_2$ receptors on CHO cells
| Compound | Molar concentration | Activity |
|---|---|---|
| 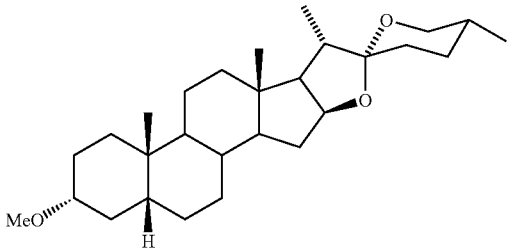 | $10^{-5}$ | Active |
| 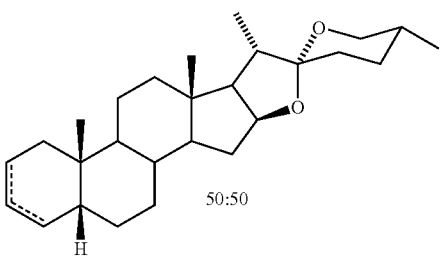 50:50 | $10^{-5}$ | Active |
| 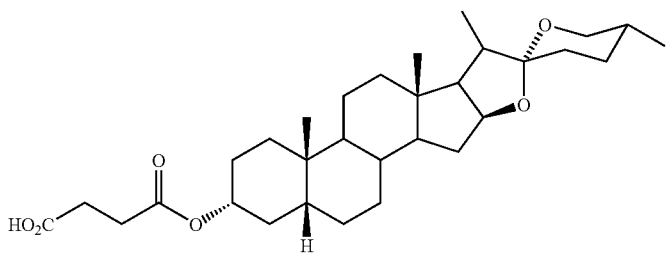 | $10^{-5}$ | Active |
| 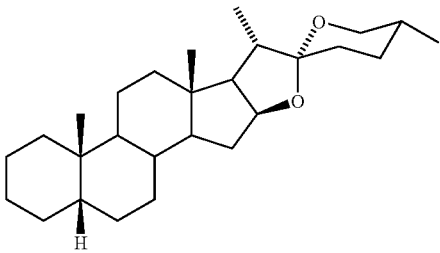 | $10^{-5}$ | Active |
| 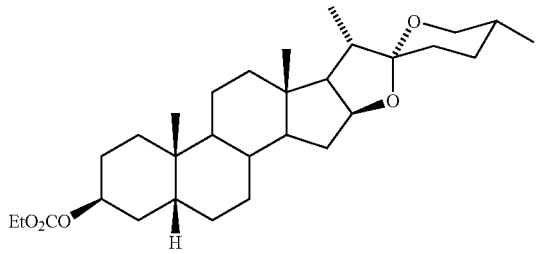 | $10^{-5}$ | Active |

TABLE 1-continued
Effects of sapogenin derivatives on the expression of $m_2$ receptors on CHO cells
| Compound | Molar concentration | Activity |
|---|---|---|
| 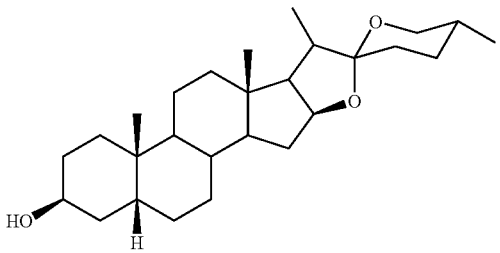 Smilagenin | $10^{-5}$ | Active |
| 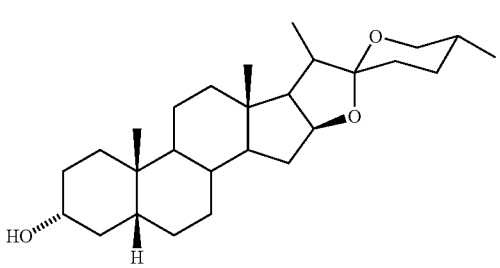 Epismilagenin | $10^{-5}$ | Active |
| 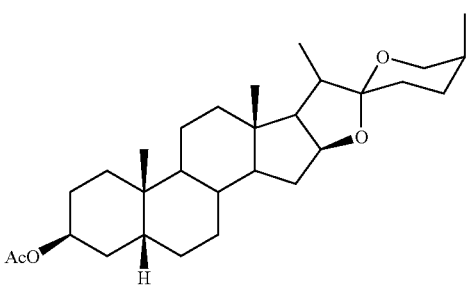 Sarsasapogenin acetate | $10^{-5}$ | Active |
| 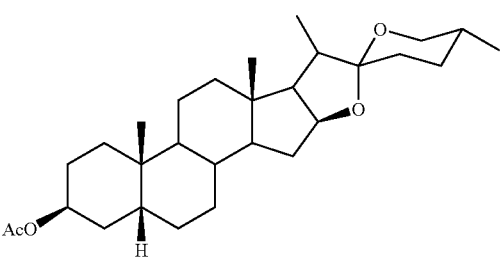 Smilagenin acetate | $10^{-5}$ | Active |
| 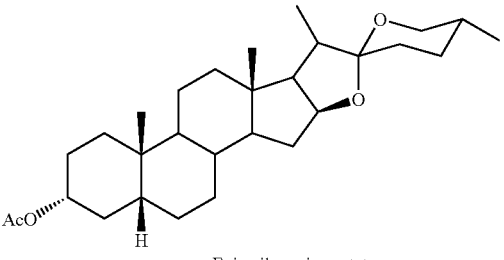 Epismilagenin acetate | $10^{-5}$ | Active |

TABLE 1-continued
Effects of sapogenin derivatives on the expression of $m_2$ receptors on CHO cells
| Compound | Molar concentration | Activity |
|---|---|---|
| 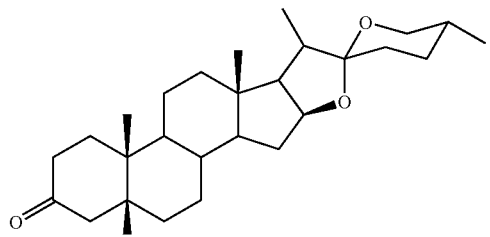<br>Smilagenone | $10^{-5}$ | Active |
| 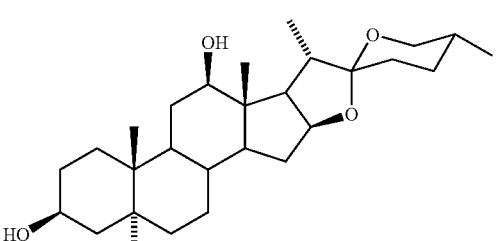<br>Rockogenin | $10^{-5}$ | Not active |
| 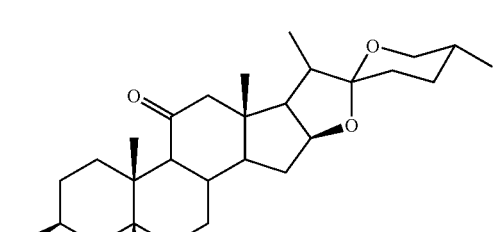<br>11-Ketotigogenin | $10^{-5}$ | Not active |
| 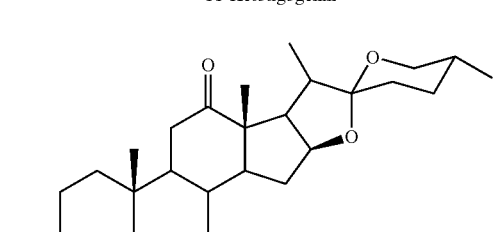<br>Hecogenin | $10^{-5}$ | Not active |
| 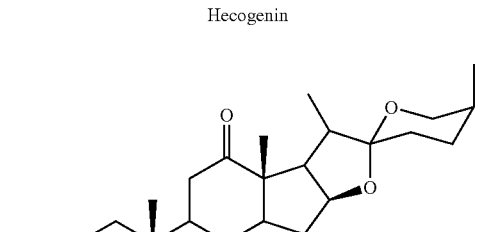<br>Sisalagenin | $10^{-5}$<br>$10^{-6}$ | Not active<br>Not active |

TABLE 1-continued
Effects of sapogenin derivatives on the expression of $m_2$ receptors on CHO cells
| Compound | Molar concentration | Activity |
|---|---|---|
| 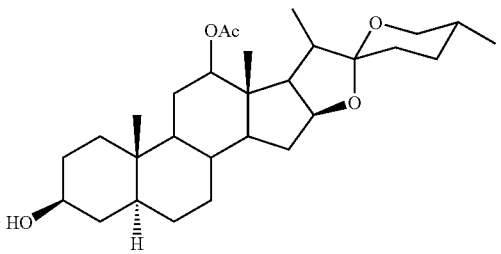<br>12-Acetoxytigogenin | $10^{-5}$ | Not active |
| 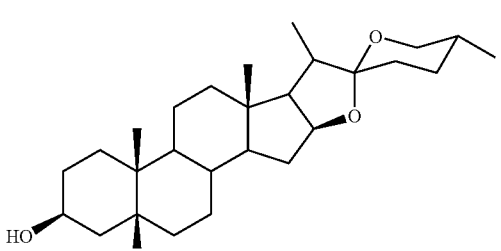<br>Tigogenin | $10^{-5}$<br>$10^{-6}$ | Not active<br>Not active |
| 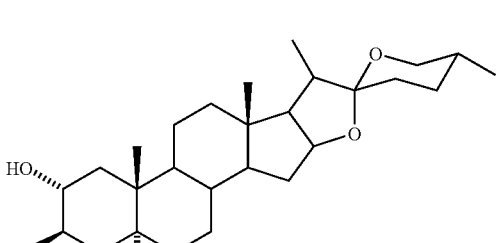<br>Gitogenin | $10^{-5}$ | Not active |
| 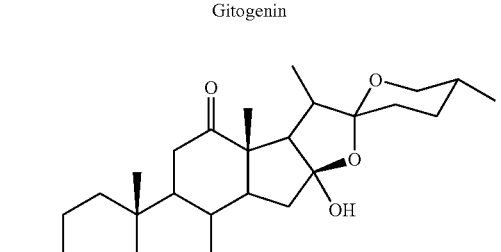<br>16α-Hydroxyhecogenin | $10^{-5}$ | Not active |
| 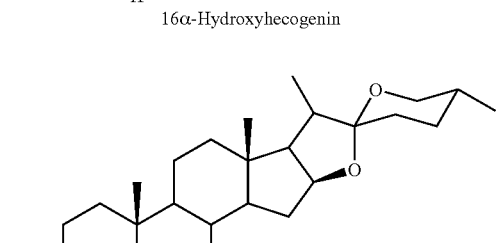<br>Diosgenin | $10^{-5}$<br>$10^{-6}$ | Not active<br>Not active |

TABLE 1-continued
Effects of sapogenin derivatives on the expression of $m_2$ receptors on CHO cells
| Compound | Molar concentration | Activity |
|---|---|---|
| 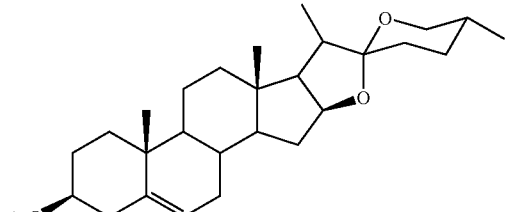<br>Diosgenin acetate | $10^{-5}$ | Not active |
| 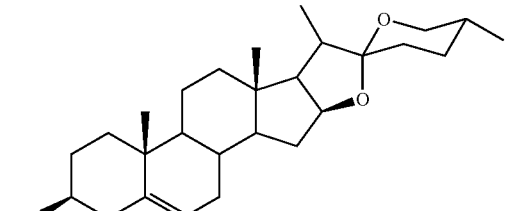<br>Diosgenin benzoate | $10^{-5}$ | Not active |
| 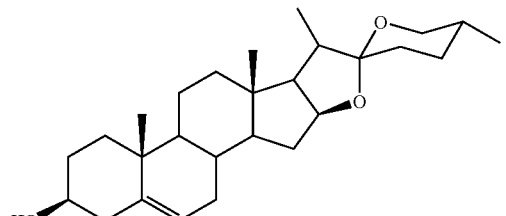<br>6-Methyldiosgenin | $10^{-5}$ | Not active |
| 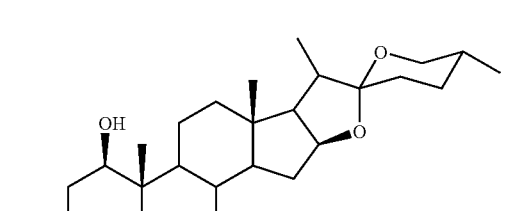<br>Ruscogenin | $10^{-5}$<br>$10^{-6}$ | Not active<br>Not active |
| 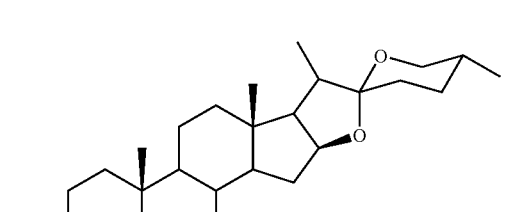<br>7-Ketodiosgenin | $10^{-5}$ | Not active |

TABLE 1-continued

Effects of sapogenin derivatives on the expression of $m_2$ receptors on CHO cells

| Compound | Molar concentration | Activity |
|---|---|---|
| 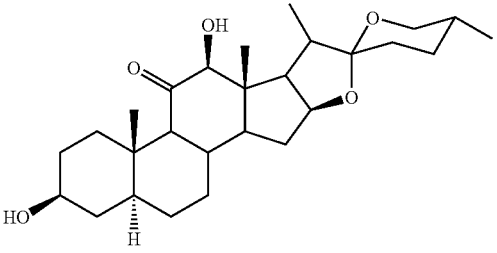<br>11-Ketorockogenin | $10^{-5}$ | Not active |
| 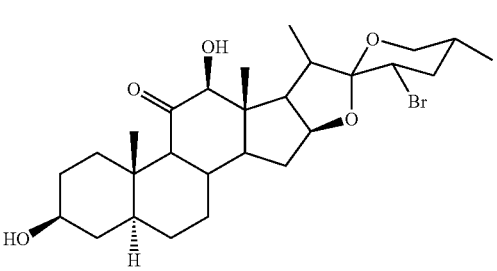<br>23-Bromo-11-ketorockogenin | $10^{-5}$ | Not active |
| 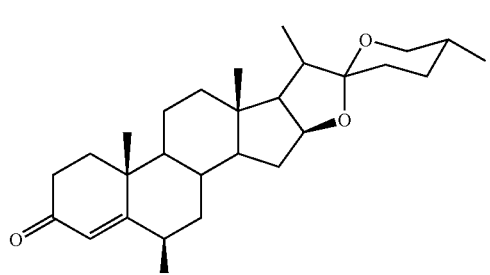<br>6β-Acetoxytigogenone | $10^{-5}$ | Not active |

Thus the experiments indicate that the sapogenin derivatives of the invention were able to increase the number of muscarinic receptors expressed on the surface of CHO cells cultured in-vitro. The effect was not antagonised by tamoxifen, indicating that the mechanism involved did not involve the oestrogen receptor.

It appears from the experimental work conducted that the compounds of this invention act to normalise muscarinic receptor number—i.e. they tend to prevent decline in receptor number with time, and also tend to restore receptor number to normal levels when given to cells in which the receptor number is depressed.

It is speculated here that the effect of the active compound claimed in this patent may operate through an effect on G protein and that the effects on receptor numbers are secondary to an effect on G-protein. When a membrane bound G-protein linked receptor is stimulated two basic sets of events are initiated: the effecter response; and the internalisation of the receptor. The subsequent processing of the receptor to the state where it is again in a form on the cell surface or other membrane surface where it can interact with another receptor ligand appears to be subject to a number of factors. A number of these factors or mechanisms appear to be G-protein linked. There is evidence that activation of $m_3$ receptors may have an effect on G-protein expression or levels. It is speculated that the actions of the compounds described in this patent may due to an interaction in the processes of receptor regeneration, G-protein linkage or G-protein homeostasis.

An alternative hypothesis is that the compounds are increasing the synthesis or release or a decreased rate of degradation of neurotropic factors such as brain derived growth factor and/or nerve growth factor. These effects on growth factors might be due to an effect of the compound on a cytosolic or nuclear receptor or the binding of a compound to a promoter region with a consequent effect directly on the rate of production of mRNA for the growth factor or as a consequence of increasing the production of another material factor such as G-protein or finally the effects may be secondary to an effect on receptor or G-protein procession.

The increased expression and/or abnormal processing of the amyloid precursor protein (APP) is associated with the formation of amyloid plaques and cerebrovascular amyloid deposits which are the major morphological hallmarks of Alzheimer's disease. Of particular interest are the processes regulating the proteolytic cleavage of APP into amyloidogenic and nonamyloidogenic fragments. The cleavage of APP by the enzyme α-secretase within the β-amyloid sequence of the protein results in the formation of a non amyloidogenic C-Terminal fragment, and the soluble APPsα fragment; this latter fragment has been shown to have neurotropic and neuroprotective activity as well as to enhance memory in mice when injected intra-cerebro-ventrically (ICV). In contrast, processing of APP by β-secretase exposes the N-terminus of β-amyloid which is released by γ-secretase cleavage at the variable C-terminus. The resulting β-amyloid peptides, which contain 39–43 amino acids, have been shown to be neurotoxic and to accumulate in plaques which interfere with inter-neurone connections.

A number of studies have shown that stimulation of the protein-kinase (PKC) linked muscarinic $M_1$ and $M_3$ receptors results in an increase in α-secretase activity. As a consequence processing of APP to APPsα with its neuroprotective effects is increased. In parallel, processing of APP by β- and γ-secretase is decreased and there is a consequential reduction of β-amyloid. Other transmitters such as nerve growth factor (NGF) and brain derived neurotropic factor (BDNF) as well as bradykinin and vasopressin may have similar effects in increasing the proportion of APP processed to APPsα. There may be a number of factors involved in the effects of NGF which may include binding of the factor to the tyrosine kinase receptor (TrkA) and the stimulation of phospholipase Cγ with subsequent phosphorylation and activation of protein kinase C (PKC) and increase in relative activity of α-secretase.

Any treatment which increases activity of protein-kinase C selectively in brain might therefore be expected to be of use in the management of Alzheimer's disease. Until recently agonists selective at the $M_1$ receptor have not been available. Non-selective agonists would be expected to stimulate pre-synaptic $M_2$ receptors which cause negative feedback and hence would further severely impair muscarinic transmission. Selective agonists at the $M_1$ receptor are now becoming available (talsaclidine) and such agents are under investigation for the treatment of AD. There is however, a substantial risk that, as with the chronic administration of any receptor agonist, the clinical benefits seen will be severely limited in terms of the size of benefit by reducing receptor numbers or reducing sensitivity and in terms of side effects due to lack of receptor specificity. Thus compounds as described in this invention, which selectively regulate muscarinic receptor number or function, would be expected to be devoid of the problems seen with a muscarinic agonist and hence have particular utility. Indeed the benefits may be seen in three parts as follows:

1. A selective increase in $M_1$ receptor numbers leading to increased synaptic transmission. Chronic administration of a selective agonist will, at best, have no adverse effect on transmission;
2. Secondary to the increased receptor numbers, an increase stimulation of PKC with a consequential increase in α-secretase activity, leading to:
2.1 A reduced production of β-amyloid and a consequent reduction of plaque formation and neuronal loss;
2.2 An increase in APPsα and a consequent improvement in cerebral function as witnessed by an improvement in short and long term memory.

In order to illustrate the invention further by way of non-limiting example, reference will now be made to the accompanying drawings and to the Example which follows; in the drawings.

Figure 4:
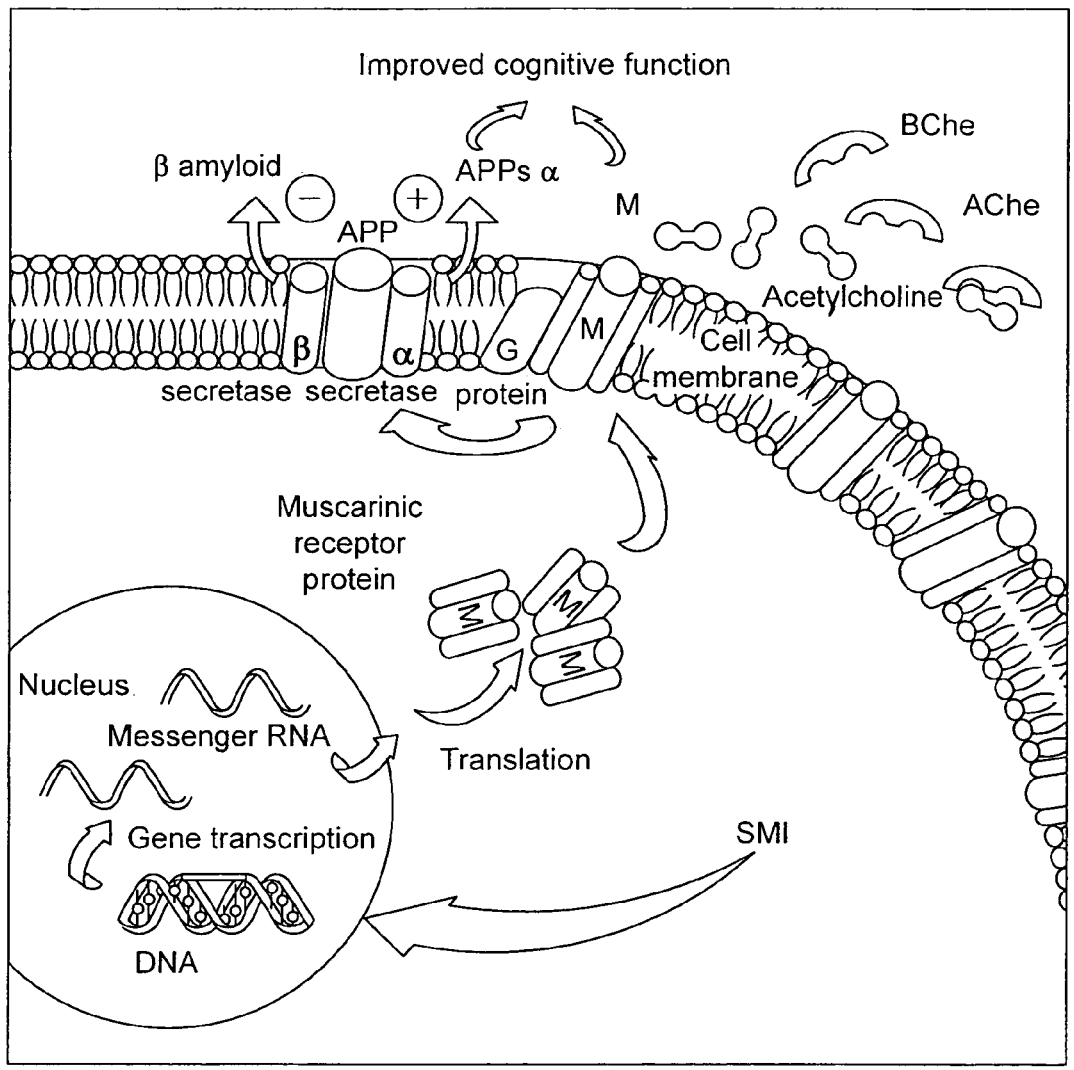
FIG. 4 illustrates a hypothetical mode of action for sapogenin derivatives.

Referring to FIG. 4, a diagrammatic representation of the function of sapogenin derivatives of the invention is shown.

It is believed that sapogenin derivatives act primarily on cell nuclei; the invention is not, however, limited to any particular mode of action. The observed increase in muscarinic receptor number consequential upon administration of sapogenin derivatives is interpreted as leading to increased expression of muscarinic receptor protein. The possible link between the secretases and β-amyloid protein formation (discussed above) is indicated in the drawing.

The following examples are provided to illustrate the invention in a non-limiting manner.

EXAMPLE 1

In a CHO cell line expressing recombinant human muscarinic receptors in vitro, the number of muscarinic receptors tends to decline with time. Sapogenin derivatives of the invention (1–10 μM) incubated for 72 hours increase muscarinic receptor density.

Methods:

Effect of sapogenin derivatives of the invention on muscarinic receptor density in CHO cells expressing recombinant human muscarinic receptors.

Chinese hamster ovary (CHO) cells expressing high levels of receptor (~2.2 pmoles receptor/mg protein) were cultured in flasks (150 ml) for 24 hours before the start of the experiment. Vehicle (DMSO) and sapogenin derivatives (at 1 and 10 μM) were added to the medium for 48 h. The culture medium was discarded, the cells scraped off and resuspended in Hanks solution, centrifuged and m-receptor levels determined by incubating with [$^3$H]-QNB for 30 min followed by liquid scintillation counting. Protein levels were determined by a micro Lowry method.

Figure 1:
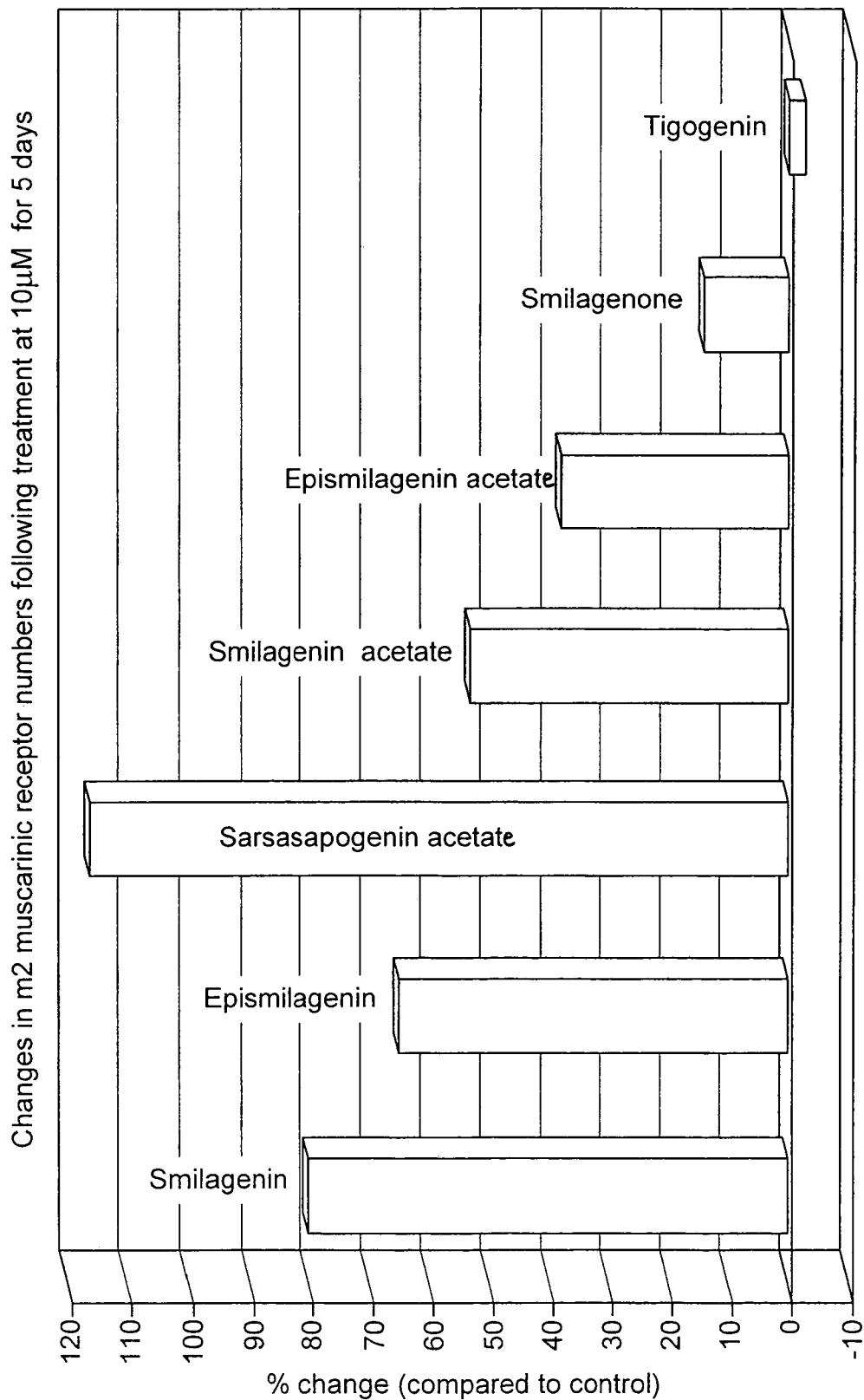
FIGS. 1, 2, 3 illustrate the results obtained in Example 1 below.
Figure 2:
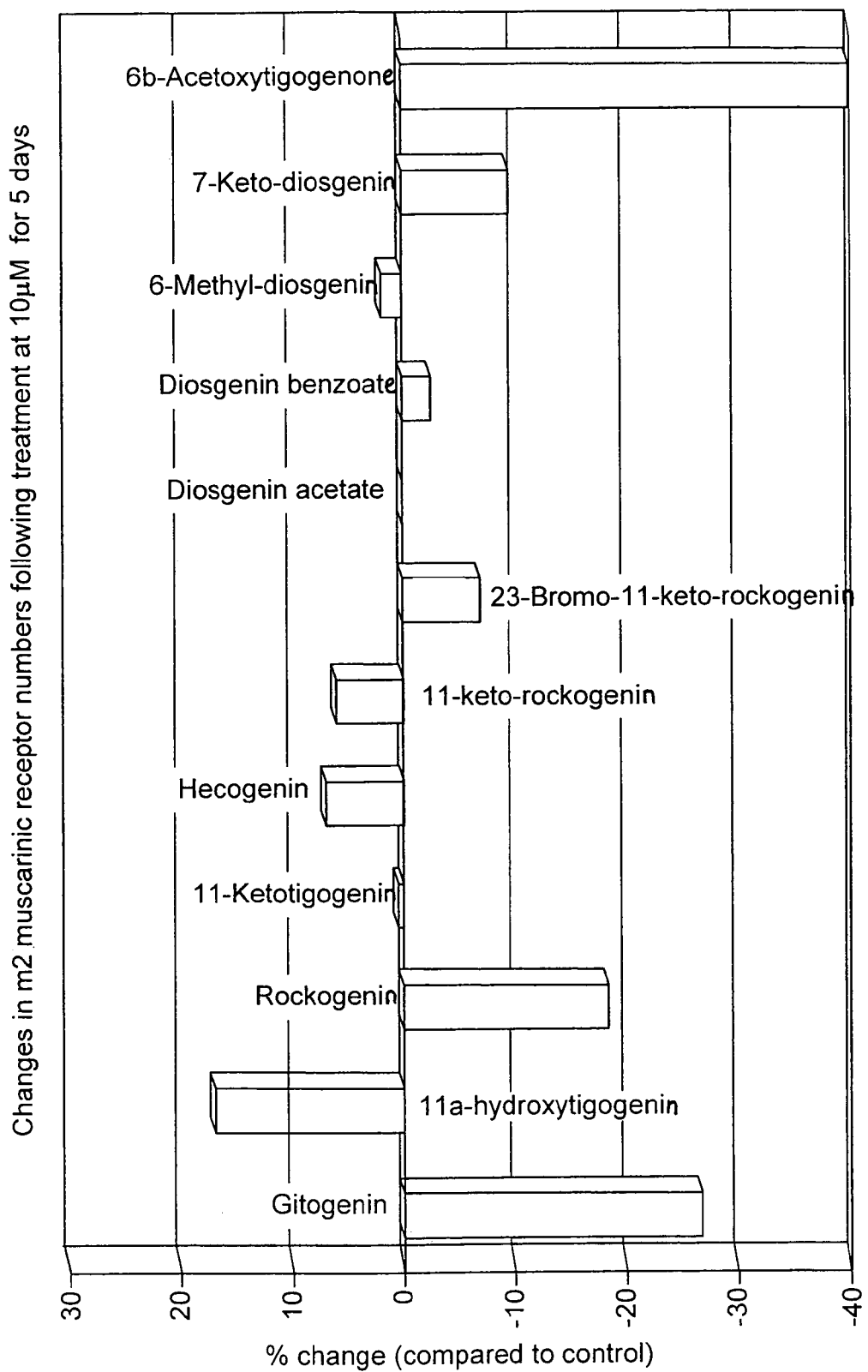
Figure 3:
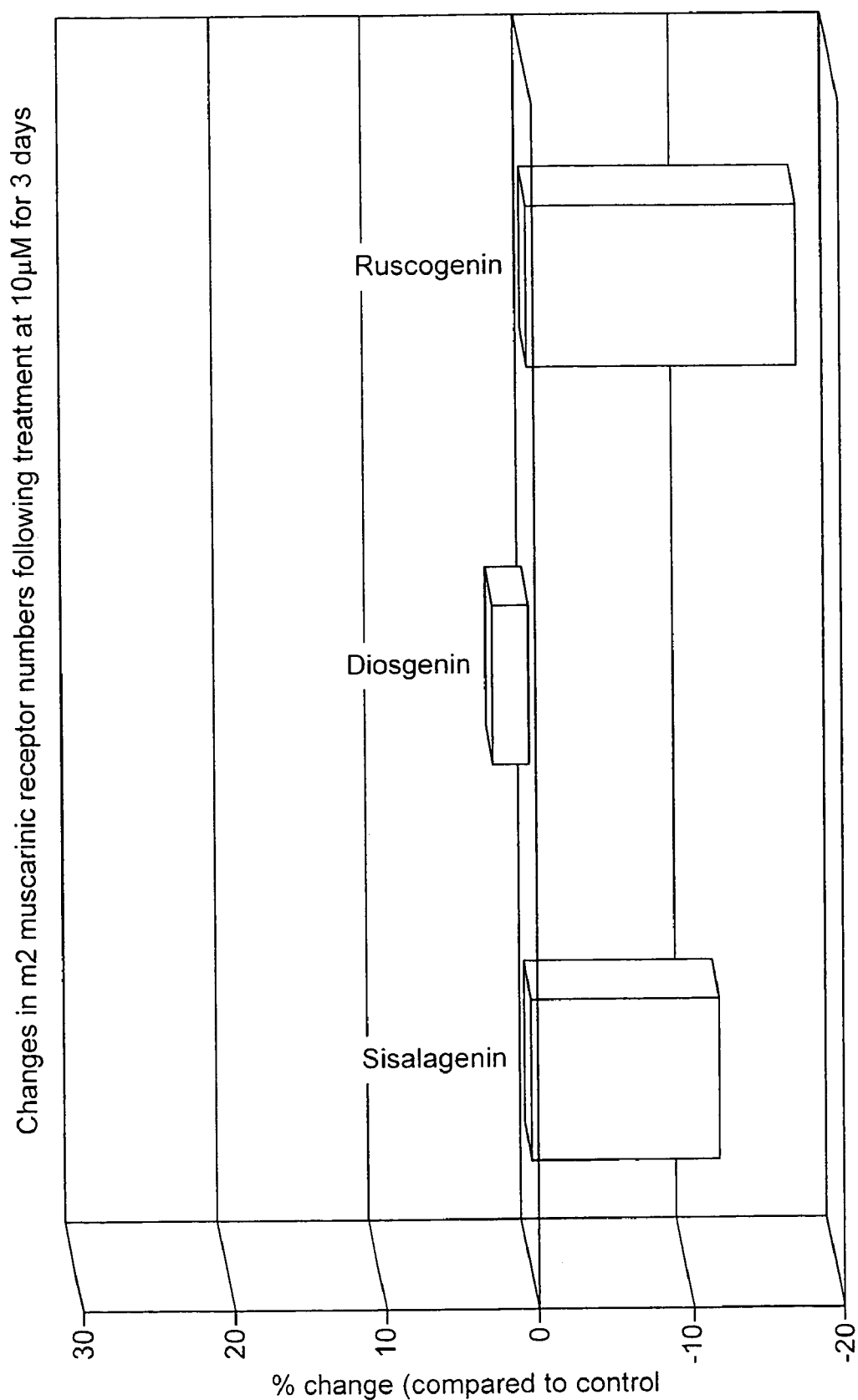

Results:

These are illustrated in FIGS. 1–3. Over the culturing period treatment with sapogenin derivatives of the invention prevents the decrease in muscarinic receptor number in a concentration-dependent manner.

EXAMPLE 2

3-O-Ethoxycarbonyl-5β, 20α, 22α, 25R-spirostan-3β-ol

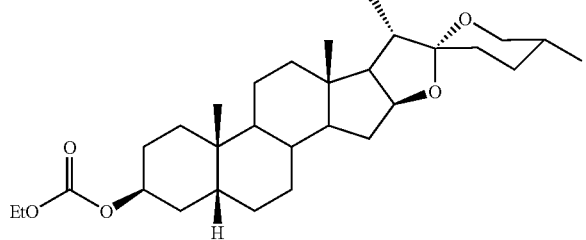

Ethyl chloroformate (1.40 g, 12.9 mmol) was added dropwise to a stirred solution of smilagenin (2.08 g, 5.0 mmol) in anhydrous dichloromethane (15 ml) and anhydrous pyridine (1.02 g, 12.9 mmol). The mixture was stirred at room temperature for 18 h and then partitioned between water (30 ml) and dichloromethane. The aqueous layer was extracted twice with dichloromethane, the combined organic layers washed with water and then dried over $MgSO_4$ (anhyd). The solvent was evaporated in vacuo to give an oil (2.1 g) that rapidly crystallised. This material was chromatographed on silica (ca. 70 g). Elution with ethyl acetate-hexane (1:9) and recrystallisation from methanol afforded white crystals of 3-O-ethoxycarbonyl-5β, 20α, 22α, 25R-spirostan-3β-ol (1.08 g):mp 154–156° C.; m/z 488 (M+ for $C_{30}H_{48}O_5$); $^1$H nmr (270 MHz, $CDCl_3$) δ 0.76 (3H, s, 18-$CH_3$), 0.78 (3H, s, 27-$CH_3$), 0.95 (3H, s, 21-$CH_3$), 0.98 (3H, s, 19-$CH_3$), 1.0–2.05 (27H, complex m, aliphatics), 1.31 (3H, t, J=7 Hz, $CO_2$—C—$CH_3$), 3.33–3.46 (2H, m, 26-$OCH_2$), 4.18 (2H, q, J=7 Hz, $CO_2CH_2$), 4.40 (1H, m, 16-OCH), 4.95 (1H, m, H-3): ppm; $^{13}$C nmr (270 MHz, $CDCl_3$) 14.3 (C—C—$O_2$C), 14.5, 16.5, 17.1, 20.9, 23.7, 25.0, 26.4, 28.8, 30.3, 30.6, 31.4, 31.8, 35.0, 35.3, 37.0, 40.0, 40.3, 40.7, 41.6, 56.4 (C-14), 62.3 (C-17), 63.6 (C—$O_2$C), 66.9 (C-26), 74.8 (C-3), 80.9 (C-16), 109.2 (C-22), 154.8 (carbonyl) ppm; $R_f$ 0.65 (silica, ethyl acetate-hexane, 1:9)

EXAMPLE 3

Epismilagenin Succinate

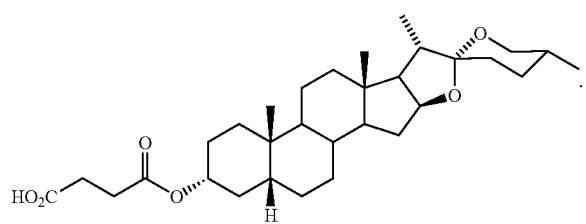

A solution of epismilagenin (200 mg, 0.48 mmol) and succinic anhydride (60 mg, 0.59 mmol) in anhydrous pyridine was stirred at room temperature under nitrogen overnight. A further portion of succinic anhydride (120 mg, 1.18 mmol) was added and the reaction stirred for a further 24 h. After addition of a further portion of succinic anhydride (120 mg, 1.18 mmol) the reaction was heated at 50° C. with stirring for a further 24 h. After the reaction was cooled, water (10 ml) was added and the aqueous solution extracted with diethyl ether (4×20 ml). The combined organic extracts were washed with water (3×20 ml), dried ($MgSO_4$ anhyd) and filtered. The solvent was evaporated in vacuo to give an orange oil (1.8 g) that was chromatographed on silica gel using ethyl acetate/petroleum ether (1:4) as eluent. Recrystallisation of the product from acetone afforded white crystals of epismilagenin succinate (87 mg); mp 180–182° C.; $^1$H nmr spectrum ($CDCl_3$, 270 MHz): partial data δ 4.75 (1H, m), 4.6 (1H, m), 3.50 (1H, dd), 3.40 (1H, t), 2.6 (4H, br dd), 0.98 (3H, d) 0.95 (3H, s), 0.80 (3H, d), 0.75 (3H, s) ppm; $^{13}$C nmr spectrum ($CDCl_3$, 68 MHz): δ 171.81, 109.27, 80.91, 74.90, 66.85, 62.25, 56.29, 41.84, 41.62, 40.65, 40.51, 40.18, 35.44, 35.01, 34.72, 32.17, 31.77, 31.38, 30.25, 29.33, 28.79, 26.93, 26.55, 23.58, 20.58, 17.11, 16.43, 14.48 ppm; $R_f$ 0.11 (silica, ethyl acetate-petroleum ether, 3:7)

What is claimed is:

1. A method of treating a condition or conditions selected from the group consisting of Alzheimer's disease, senile dementia of the Alzheimer's type (SDAT), Parkinson's disease, Lewi body dementia, postural hypotension, autism, chronic fatigue syndrome, Myasthenia Gravis, and learning deficit and memory loss which comprises administering to a human an effective amount of a sapogenin derivative of general formula (I) or (II):

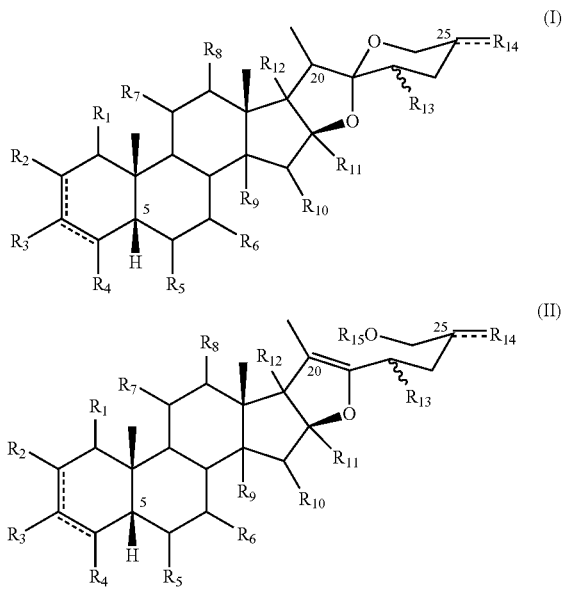

including all stereoisomers and racemic mixtures thereof, a pharmaceutically acceptable salt thereof, or a pharmaceutically acceptable pro-drug precursor of any of the compounds of general formula (I) or (II), wherein:

in the general formula (I):

$R_1$, $R_2$, $R_3$, $R_4$, $R_5$, $R_6$, $R_7$, $R_8$, $R_{10}$, are, independently of each other, either H, OH, =O, and OR where R=optionally substituted alkyl, optionally substituted acyl, optionally substituted carbamoyl, alkoxycarbonyl;

$R_9$, $R_{12}$, $R_{11}$, $R_{13}$ can be either a H, OH, OR where R=optionally substituted alkyl, optionally substituted acyl, optionally substituted carbamoyl, alkoxycarbonyl;

$R_{14}$=optionally substituted alkyl group ═══represents an optional double bond, but excluding where simultaneously;

$R_1$=$R_2$=$R_4$=$R_5$=$R_6$=$R_7$=$R_8$=$R_{10}$=$R_{11}$=$R_9$=$R_{12}$=$R_{13}$=H, no double bonds are present the methyl group at C20 is α;

and wherein in the general formula (II):

$R_1$, $R_2$, $R_3$, $R_4$, $R_5$, $R_6$, $R_7$, $R_8$, $R_{10}$, are, independently of each other, either H, OH, =O, or OR where R=optionally substituted alkyl, optionally substituted acyl, optionally substituted carbamoyl, alkoxycarbonyl;

$R_9$, $R_{12}$, $R_{13}$ can be either a H, OH, OR where R=optionally substituted alkyl, optionally substituted acyl, optionally substituted carbamoyl, alkoxycarbonyl;

$R_{14}$=optionally substituted alkyl group;

$R_{15}$=H, optionally substituted alkyl, optionally substituted acyl, or glucosyl;

═══represents an optional double bond.

2. A method according to claim 1, wherein in the general formula (I)

$R_4$, $R_9$, $R_{12}$, $R_{13}$=H $R_1$, $R_2$, $R_3$, $R_5$, $R_6$, $R_7$, $R_8$, $R_{10}$, are independently of each other either H, OH, =O, OR where R=optionally substituted alkyl, optionally substituted acyl, optionally substituted carbamoyl, alkoxycarbonyl;

$R_{11}$=H, OH, OR where R=optionally substituted alkyl, optionally substituted acyl, optionally substituted carbamoyl, alkoxycarbonyl;

$R_{14}$=alkyl group and ==== represents an optional double bond.

3. A method according to claim 1, wherein in the general formula (I):

$R_1$=$R_2$=$R_4$=$R_5$=$R_6$=$R_7$=$R_8$=$R_{10}$=$R_{11}$=$R_9$=$R_{12}$=$R_{13}$=H, $R_3$=H, —OH, —OMe, —OCOCH$_3$, =O, —O—CO$_2$Et, —O—CO—(CH$_2$)$_2$—CO$_2$H;

$R_{14}$=CH$_3$.

4. A method according to claim 1, wherein in the general formula (II):

$R_4$, $R_9$, $R_{12}$, $R_{13}$=H $R_1$, $R_2$, $R_3$, $R_5$, $R_6$, $R_7$, $R_8$, $R_{10}$, can be independently of each other either H, OH, =O, OR where R=optionally substituted alkyl, optionally substituted acyl, optionally substituted carbamoyl, alkoxycarbonyl;

$R_{11}$=H, OH, OR where R=optionally substituted alkyl, optionally substituted acyl, optionally substituted carbamoyl, alkoxycarbonyl;

$R_{14}$=alkyl group $R_{15}$=H, optionally substituted alkyl, optionally substituted acyl, or glucosyl;

and ==== represents an optional double bond.

5. A method according to claim 1, wherein the compound is selected from 3-methoxy-sarsasapogenin, 3-methoxy-epismilagenin, smilagenin cathylate epismilagenin succinate, epismilagenin, sarsasapogenin acetate, smilagenin acetate, epismilagenin acetate, smilagenone, and derivatives of smilagenin and sarsasapogenin in which there is no substituent at C3 and there is a single bond between C2 and C3 and between C3 and C4 or there is a doable bond between C2 and C3 or between C3 and C4.

6. A method according to claim 1, wherein said human is suffering from age-related cognitive dysfunction.

7. A method according to claim 1, wherein said cognitive disfunction is selected from the group consisting of: Alzheimer's disease or senile dementia of the Azheimer's type.

8. A method according to claim 1, wherein the compound of formula (I) or (II) or a pro-drug or salt thereof is administered in the form of a pharmaceutical composition, foodstuff, food supplement or beverage.

9. A method of enhancing cognitive function, which comprises administering to a human an effective dose of a pharmaceutical composition selected from the group consisting of:

a) compounds of formula (I) as defined in claim 1, b) compounds of formula (II) as defined in claim 1, c) pharmaceutically acceptable salts of said compounds of formula (I) or formula (II), d) a pharmaceutically acceptable pro-drug precursor of any of said compounds of formula (I) or formula (II), and e) mixtures of the compounds as defined in a through d hereof.

10. A method according to claim 9, wherein said pharmaceutical composition is administered in the form of a foodstuff, food supplement or beverage.

11. A method of increasing the muscarinic, nicotinic or dopamine receptor number or enhancing the function of muscarinic, nicotinic or dopamine receptors for treating a condition or conditions selected from the group consisting of Alzheimer's disease, senile dementia of the Alzheimer's type (SDAT), Parkinson's disease, Lewi body dementia, postural hypotension, autism, chronic fatigue syndrome, Myasthenia Gravis, and learning deficit and memory loss which comprises administering to a human an effective amount of a sapogenin derivative of general formula (I) or (II):

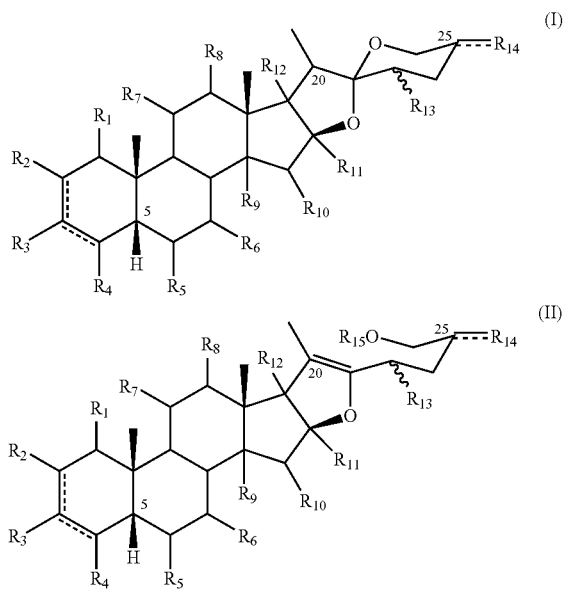

including all stereoisomers and racemic mixtures thereof, a pharmaceutically acceptable salt thereof, or a pharmaceutically acceptable pro-drug precursor of any of the compounds of general formula (I) or (II), wherein:

in the general formula (I):

$R_1$, $R_2$, $R_3$, $R_4$, $R_5$, $R_6$, $R_7$, $R_8$, $R_{10}$, are, independently of each other, either H, OH, =O, and OR where R=optionally substituted alkyl, optionally substituted acyl, optionally substituted carbamoyl, alkoxycarbonyl;

$R_9$, $R_{12}$, $R_{11}$, $R_{13}$ can be either a H, OH, OR where R=optionally substituted alkyl, optionally substituted acyl, optionally substituted carbamoyl, alkoxycarbonyl;

$R_{14}$=optionally substituted alkyl group ==== represents an optional double bond, but excluding where simultaneously;

$R_1$=$R_2$=$R_4$=$R_5$=$R_6$=$R_7$=$R_8$=$R_{10}$=$R_{11}$=$R_9$=$R_{12}$=$R_{13}$=H, $R_3$=β—OH, $R_{14}$=CH$_3$ no double bonds are present the methyl group at C20 is α;

and wherein in the general formula (II):

$R_1$, $R_2$, $R_3$, $R_4$, $R_5$, $R_6$, $R_7$, $R_8$, $R_{10}$, are, independently of each other, either H, OH, =O, or OR where R=optionally substituted alkyl, optionally substituted acyl, optionally substituted carbamoyl, alkoxycarbonyl;

$R_9$, $R_{12}$, $R_{13}$ can be either a H, OH, OR where R=optionally substituted alkyl, optionally substituted acyl, optionally substituted carbamoyl, alkoxycarbonyl;

$R_{14}$=optionally substituted alkyl group;

$R_{15}$=H, optionally substituted alkyl, optionally substituted acyl, or glucosyl;

==== represents an optional double bond.

12. A method according to claim 11 wherein in the general formula (I):

$R_4$, $R_9$, $R_{12}$, $R_{13}$=H $R_1$, $R_2$, $R_3$, $R_5$, $R_6$, $R_7$, $R_8$, $R_{10}$, are independently of each other either H, OH, =O, OR where R=optionally substituted alkyl, optionally substituted acyl, optionally substituted carbamoyl, alkoxycarbonyl;

$R_{11}$=H, OH, OR where R=optionally substituted alkyl, optionally substituted acyl, carbamoyl, alkoxycarbonyl;

$R_{14}$=alkyl group and ≈≈≈≈represents an optional double bond.

13. A method according to claim 11, wherein in the general formula (I):

$R_1=R_2=R_4=R_5=R_6=R_7=R_8=R_{10}=R_{11}=R_9=R_{12}=R_{13}$=H, $R_3$=H, —OH, —OMe, —OCOCH$_3$, =O, —O—CO$_2$Et, —O—CO—(CH$_2$)$_2$—CO$_2$H;

$R_{14}$=CH$_3$.

14. A method according to claim 11, wherein in the general formula (II):

$R_4$, $R_9$, $R_{12}$, $R_{13}$=H $R_1$, $R_2$, $R_3$, $R_5$, $R_6$, $R_7$, $R_8$, $R_{10}$, are independently of each other either H, OH, =O, OR where R=optionally substituted alkyl, optionally substituted acyl, optionally substituted carbamoyl, alkoxycarbonyl;

$R_{11}$=H, OH, OR where R=optionally substituted alkyl, optionally substituted acyl, optionally substituted carbamoyl, alkoxycarbonyl;

$R_{14}$=alkyl group $R_{15}$=H, optionally substituted alkyl, optionally substituted acyl, or glucosyl;

and ≈≈≈≈represents an optional double bond.

15. A method according to claim 11, wherein the compound is selected from 3-methoxy-sarsasapogenin, 3-methoxy-epismilagenin, smilagenin cathylate epismilagenin succinate, epismilagenin, sarsasapogenin acetate, smilagenin acetate, epismilagenin acetate, smilagenone, and derivatives of smilagenin and sarsasapogenin in which there is no substituent at C3 and there is a single bond between C2 and C3 and between C3 and C4 or there is a double bond between C2 and C3 or between C3 and C4.

16. A method according to claim 11, wherein the compound of formula (I) or (II) or a pro-drug or salt thereof is administered in the form of a pharmaceutical composition, foodstuff, food supplement or beverage.

17. A method of treating a condition or conditions selected from the group consisting of Alzheimer's disease, senile dementia of the Alzheimer's type (SDAT), Parkinson's disease, Lewi body dementia, postural hypotension, autism, chronic, fatigue syndrome, Myasthenia Gravis, and learning deficit and memory loss wherein said condition or conditions are characterized by the presence of neurofibrillary tangles and/or β-amyloid plaques in a human, which comprises administering to the said human an effective amount of a sapogenin or sapogenin derivative of general formula (I) or (II)

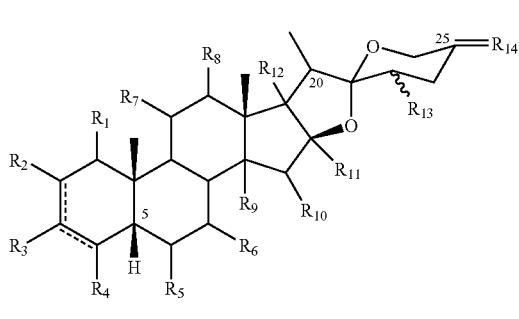

(I)

-continued

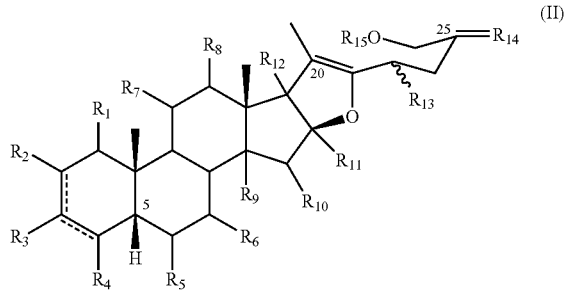

(II)

including all stereoisomers and racemic mixtures thereof, a pharmaceutically acceptable salt thereof, or a pharmaceutically acceptable pro-drug precursor of any of the compounds of general formula (I) or (II), wherein:

in the general formula (I):

$R_1$, $R_2$, $R_3$, $R_4$, $R_5$, $R_6$, $R_7$, $R_8$, $R_{10}$, are, independently of each other, either H, OH, =O, and OR where R=optionally substituted alkyl, optionally substituted acyl, optionally substituted carbamoyl, alkoxycarbonyl;

$R_9$, $R_{12}$, $R_{11}$, $R_{13}$ can be either a H, OH, OR where R=optionally substituted alkyl, optionally substituted acyl, optionally substituted carbamoyl, alkoxycarbonyl;

$R_{14}$=optionally substituted alkyl group

≈≈≈≈represents an optional double bond, but excluding where simultaneously;

$R_1=R_2$—$R_4=R_6=R_7=R_8=R_{10}=R_{11}=R_9=R_{12}=R_{13}$=H, $R_3$=βOH, $R_{14}$=CH$_3$ no double bonds are present the methyl group at C20 is α;

and wherein in the general formula (II):

$R_1$, $R_2$, $R_3$, $R_4$, $R_5$, $R_6$, $R_7$, $R_8$, $R_{10}$, are, independently of each other, either H, OH, =O, or OR where R=optionally substituted alkyl, optionally substituted acyl, optionally substituted carbamoyl, alkoxycarbonyl;

$R_9$, $R_{12}$, $R_{11}$, $R_{13}$ can be either a H, OH, OR where R=optionally substituted alkyl, optionally substituted acyl, optionally substituted carbamoyl, alkoxycarbonyl;

$R_{14}$=optionally substituted alkyl group;

$R_{15}$=H, optionally substituted alkyl, optionally substituted acyl, or glucosyl;

≈≈≈≈represents an optional double bond.

18. A method according to claim 17, wherein in the general formula (I):

$R_4$, $R_9$, $R_{12}$, $R_{13}$=H $R_1$, $R_2$, $R_3$, $R_5$, $R_6$, $R_7$, $R_8$, $R_{10}$, are independently of each other either H, OH, =O, OR where R=optionally substituted alkyl, optionally substituted acyl, optionally substituted carbamoyl, alkoxycarbonyl;

$R_{11}$=H, OH, OR where R=optionally substituted alkyl, optionally substituted acyl, optionally substituted carbamoyl, alkoxycarbonyl;

$R_{14}$=alkyl group and ≈≈≈≈represents an optional double bond.

19. A method according to claim 17, wherein in the general formula (I):

$R_1=R_2=R_4=R_5=R_6=R_7=R_8=R_{10}=R_{11}=R_9=R_{12}=R_{13}$=H, $R_3$=H, —OH, —OMe, —OCOCH$_3$, =O, —O—CO$_2$Et, —O—CO—(CH$_2$)$_2$—CO$_2$H;

$R_{14}$=CH$_3$.

20. A method according to claim 17, wherein in the general formula (II):

$R_4, R_9, R_{12}, R_{13}$=H $R_1, R_2, R_3, R_5, R_6, R_7, R_8, R_{10}$, are independently of each other either H, OH, =O, OR where R=optionally substituted alkyl, optionally substituted acyl, optionally substituted carbamoyl, alkoxycarbonyl;

$R_{11}$=H, OH, OR where R=optionally substituted alkyl, optionally substituted acyl, carbamoyl, alkoxycarbonyl;

$R_{14}$=optionally substituted alkyl group $R_{15}$=H, optionally substituted alkyl, optionally substituted acyl, or glucosyl;

and - - - - represents an optional double bond.

21. A method according to claim 17, wherein the compound is selected from 3-methoxy-sarsasapogenin, 3-methoxy-epismilagenin, smilagenin cathylate epismilagenin succinate, epismilagenin, sarsasapogenin acetate, smilgenin acetate, epismilagenin acetate, smilagenone, and derivatives of smilagenin and sarsasapogenin in which there is no substituent at C3 and there is a single bond between C2 and C3 and between C3 and C4 or there is a double bond between C2 and C3 or between C3 and C4.

22. A method according to claim 17, wherein the compound of formula (I) or (II) or a pro-drug or salt thereof is administered in the form of a pharmaceutical composition, foodstuff, food supplement or beverage.

23. A pharmaceutical composition for treating a condition characterized by the presence of neurofibrillary tangles and/or β-amyloid plaques in a human suffering therefrom, which comprises a physiologically effective amount of a compound of formula (I) or (II) or a pro-drug or salt thereof as defined in claim 1, and one or more pharmaceutically acceptable carriers, diluents or excipients.

24. A foodstuff, food supplement or beverage for treating a condition characterized by the presence of neurofibrillary tangles and/or β-amyloid plaques in a human suffering therefrom, which comprises a physiologically effective amount of a compound of formula (I) or (II) or a pro-drug or salt thereof as defined in claim 1, and an edible carrier, diluent or excipient.

25. A pharmaceutical composition according to claim 23, wherein the compound of formula (I) or (II) or pro-drug, or salt thereof is in the form of an extract derived form a plant of the genus *Smilax, Asparagus, Anemarrhena, Yucca* or *Agave*.

26. A foodstuff, food supplement or beverage according to claim 24, wherein the compound of formula (I) or (II) or pro-drug or salt thereof is in the form of an extract derived from a plant of the genus *Smilax, Asparagus, Anemarrhena, Yucca* or *Agave*.

27. The method of claim 1 wherein the sapogenin derivative is selected from compounds having the following structural formulae:

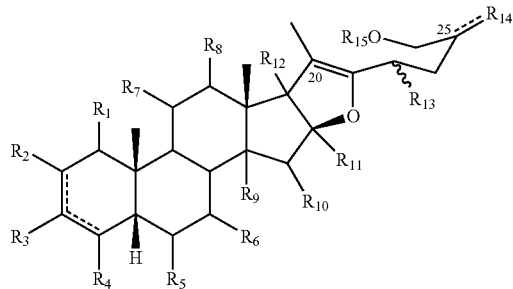

-continued

-continued
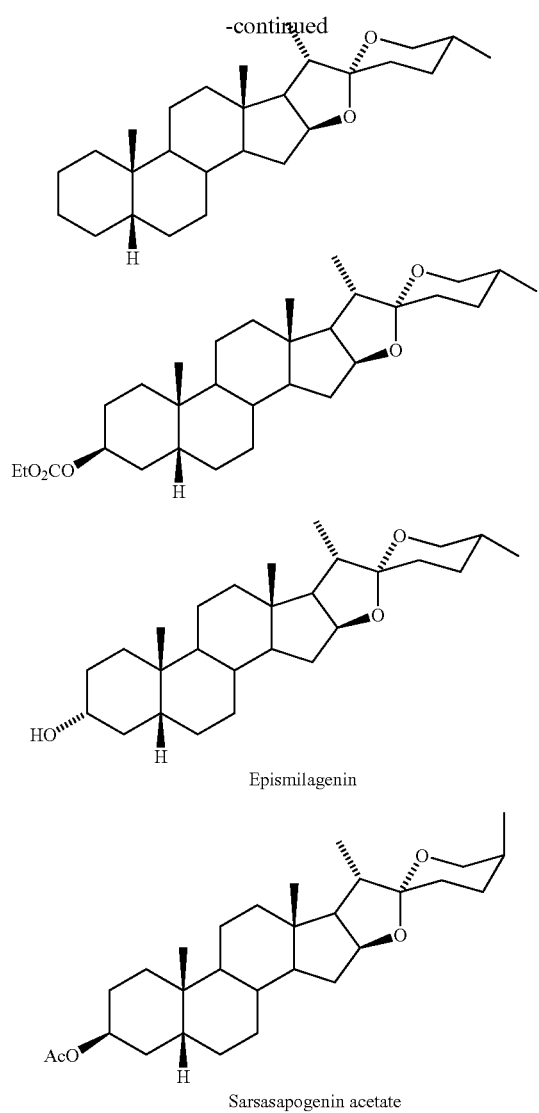
Epismilagenin
Sarsasapogenin acetate
-continued
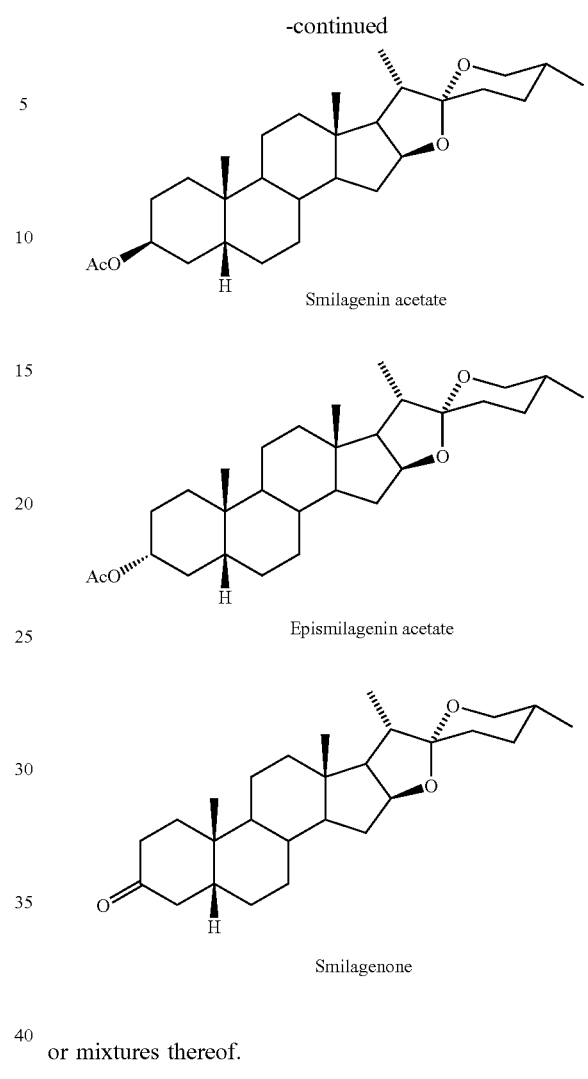
Smilagenin acetate
Epismilagenin acetate
Smilagenone
or mixtures thereof.
* * * * *

UNITED STATES PATENT AND TRADEMARK OFFICE
CERTIFICATE OF CORRECTION

PATENT NO. : 7,138,427 B2
APPLICATION NO. : 10/109095
DATED : November 21, 2006
INVENTOR(S) : Paul Barraclough et al.

It is certified that error appears in the above-identified patent and that said Letters Patent is hereby corrected as shown below:

On the Title Page:

Item (73), "PLC." should be -- PLC --.

Item (65), please add -- US 2003/0004147 A1, Jan. 2, 2003 --.

Item (65), please add -- US 2006/0100184 A9, May 11, 2006 --.

At Column 26, lines 44-45,
"-$R_1= R_2= R_4= R_5= R_6= R_7= R_8= R_{10}=R_{11}= R_9= R_{12}= R_{13}= H$,
no double bonds are present"
should be
-- -$R_1= R_2= R_4= R_5= R_6= R_7= R_8= R_{10}=R_{11}= R_9= R_{12}= R_{13}= H$,
-$R_3 = \beta\text{-OH}$,
-$R_{14} = CH_3$
-no double bonds are present--.

At Column 26, line 53, "$R_{12}, R_{13}$" should be -- $R_{12}, R_{11}, R_{13}$, --.

At Column 27, line 21, "$R_{14}$=alkyl group" should be -- $R_{14}$=optionally substituted alkyl group --.

At Column 27, line 27, "cathylate" should be -- cathylate, --.

At Column 27, line 32, "doable" should be -- double --.

At Column 27, line 37, " Azheimer's" should be -- Alzheimer's --.

At Column 28, lines 42-43, "simultaneously;" should be -- simultaneously: --.

At Column 28, line 55, "$R_{12}, R_{13}$" should be -- $R_{12}, R_{11}, R_{13}$ --.

At Column 28, line 63, "claim 11" should be -- claim 11, --.

At Column 29, line 26, "$R_{14}$=alkyl group" should be -- $R_{14}$=optionally substituted alkyl group --.

At Column 29, line 32, "cathylate" should be -- cathylate, --.

At Column 29, line 47, "chronic," should be -- chronic --.

UNITED STATES PATENT AND TRADEMARK OFFICE
CERTIFICATE OF CORRECTION

PATENT NO. : 7,138,427 B2
APPLICATION NO. : 10/109095
DATED : November 21, 2006
INVENTOR(S) : Paul Barraclough et al.

It is certified that error appears in the above-identified patent and that said Letters Patent is hereby corrected as shown below:

At Column 29, Formula 1,

" 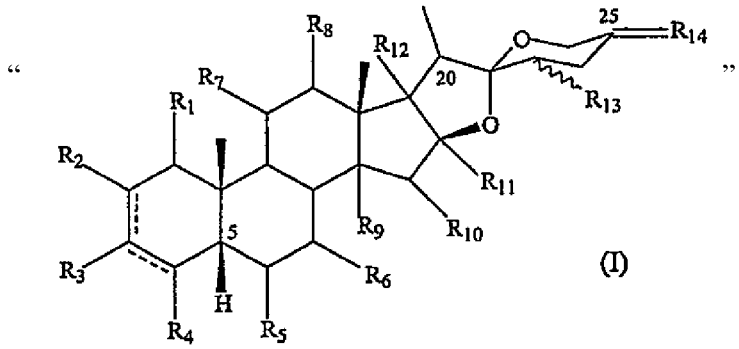 "

should be

-- 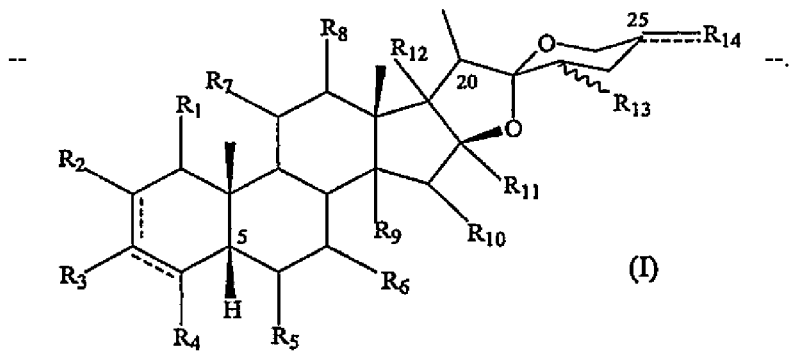 --.

At Column 30, Formula II,

" 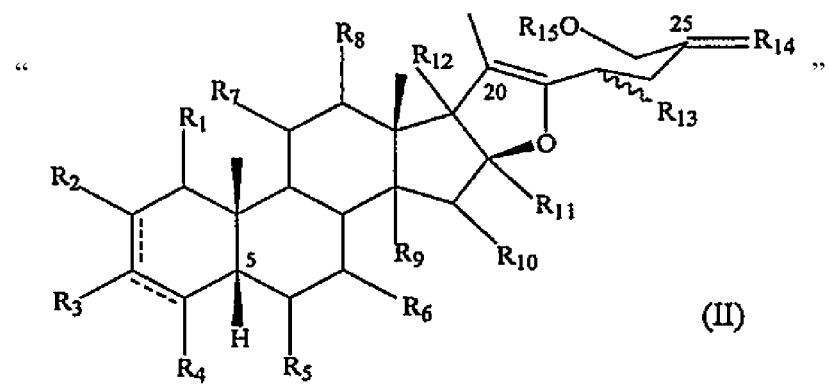 "

UNITED STATES PATENT AND TRADEMARK OFFICE
CERTIFICATE OF CORRECTION

PATENT NO. : 7,138,427 B2
APPLICATION NO. : 10/109095
DATED : November 21, 2006
INVENTOR(S) : Paul Barraclough et al.

It is certified that error appears in the above-identified patent and that said Letters Patent is hereby corrected as shown below:

should be

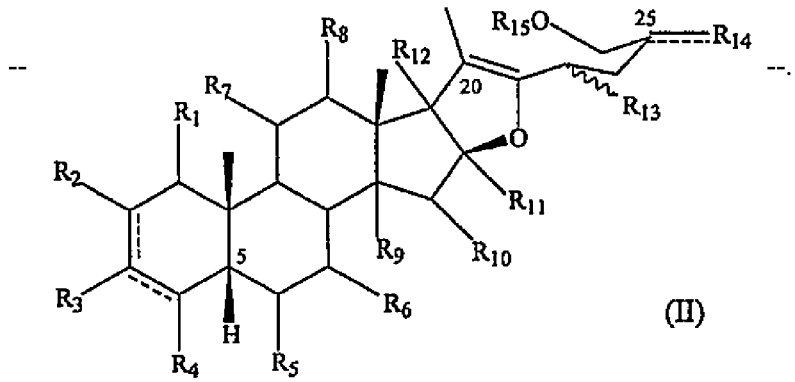

-- -- .

(II)

At Column 30, line 33, "=$R_2$-$R_4$=$R_6$=" should be -- =$R_2$=$R_4$=$R_5$=$R_6$= --.

At Column 31, line 17, "cathylate" should be -- cathylate, --.

At Column 31, line 18, "smilgenin" should be -- smilagenin --.

At Column 31, line 43, "form a plant" should be -- from a plant --.

Signed and Sealed this

Third Day of July, 2007

JON W. DUDAS
*Director of the United States Patent and Trademark Office*